(12) United States Patent
Seehra et al.

(10) Patent No.: US 9,493,556 B2
(45) Date of Patent: Nov. 15, 2016

(54) ACTRIIA BINDING AGENTS AND USES THEREOF

(71) Applicant: Acceleron Pharma, Inc., Cambridge, MA (US)

(72) Inventors: Jasbir Seehra, Lexington, MA (US); Erik Martinez-Hackert, Okemos, MI (US)

(73) Assignee: Acceleron Pharma Inc., Cambridge, MA (US)

(*) Notice: Subject to any disclaimer, the term of this patent is extended or adjusted under 35 U.S.C. 154(b) by 0 days.

(21) Appl. No.: 14/163,955

(22) Filed: Jan. 24, 2014

(65) Prior Publication Data

US 2014/0199317 A1    Jul. 17, 2014

Related U.S. Application Data

(63) Continuation of application No. 13/291,958, filed on Nov. 8, 2011, now abandoned.

(60) Provisional application No. 61/411,396, filed on Nov. 8, 2010.

(51) Int. Cl.
| | | |
|---|---|---|
| A61K 39/395 | (2006.01) | |
| C07K 16/00 | (2006.01) | |
| C07K 16/18 | (2006.01) | |
| C07K 16/22 | (2006.01) | |
| C07K 16/28 | (2006.01) | |

(52) U.S. Cl.
CPC ........... *C07K 16/22* (2013.01); *C07K 16/2863* (2013.01); *C07K 2299/00* (2013.01); *C07K 2317/55* (2013.01); *C07K 2317/56* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,973,577 A | 11/1990 | Vale, Jr. et al. | |
| 5,118,667 A | 6/1992 | Adams et al. | |
| 5,658,876 A | 8/1997 | Crowley et al. | |
| 5,703,043 A | 12/1997 | Celeste et al. | |
| 5,760,010 A | 6/1998 | Klein | |
| 5,808,007 A | 9/1998 | Lee et al. | |
| 5,824,637 A | 10/1998 | Crowley et al. | |
| 5,847,078 A | 12/1998 | Eto et al. | |
| 5,885,794 A | 3/1999 | Mathews et al. | |
| 6,004,780 A | 12/1999 | Soppet et al. | |
| 6,034,062 A | 3/2000 | Thies et al. | |
| 6,093,547 A | 7/2000 | Jin et al. | |
| 6,132,988 A | 10/2000 | Sugino et al. | |
| 6,162,896 A | 12/2000 | Mathews et al. | |
| 6,287,816 B1 | 9/2001 | Rosen et al. | |
| 6,440,930 B1 | 8/2002 | Rinella, Jr. | |
| 6,451,334 B2 | 9/2002 | Perrine | |
| 6,537,966 B1 | 3/2003 | Duan et al. | |
| 6,548,634 B1 | 4/2003 | Ballinger et al. | |
| 6,599,876 B2 | 7/2003 | Kojima | |
| 6,605,699 B1 | 8/2003 | Ni et al. | |
| 6,632,180 B1 | 10/2003 | Laragh | |
| 6,656,475 B1 | 12/2003 | Lee et al. | |
| 6,656,708 B1 | 12/2003 | Yu et al. | |
| 6,692,925 B1 | 2/2004 | Miyazono et al. | |
| 6,696,260 B1 | 2/2004 | Lee et al. | |
| 6,777,205 B1 | 8/2004 | Carcagno et al. | |
| 6,835,544 B2 | 12/2004 | Mathews et al. | |
| 6,891,082 B2 | 5/2005 | Lee et al. | |
| 6,914,128 B1 | 7/2005 | Salfeld et al. | |
| 7,052,873 B2 | 5/2006 | Tsuchiya | |
| 7,192,717 B2 | 3/2007 | Hill et al. | |
| 7,202,210 B2 | 4/2007 | Wolfman et al. | |
| 7,261,893 B2 | 8/2007 | Veldman et al. | |
| 7,320,789 B2 | 1/2008 | Dunham et al. | |
| 7,560,441 B2 | 7/2009 | Wolfman et al. | |
| 7,612,041 B2 | 11/2009 | Knopf et al. | |
| 7,709,605 B2 | 5/2010 | Knopf et al. | |
| 7,842,663 B2 | 11/2010 | Knopf et al. | |
| 7,893,213 B2 | 2/2011 | Mathews et al. | |
| 7,919,296 B2 | 4/2011 | Wang | |
| 7,947,646 B2 | 5/2011 | Sun et al. | |
| 7,951,771 B2 | 5/2011 | Knopf et al. | |
| 7,968,091 B2 | 6/2011 | Woolf et al. | |
| 7,988,973 B2 | 8/2011 | Sherman | |
| 8,007,809 B2 | 8/2011 | Sherman | |
| 8,058,229 B2 | 11/2011 | Seehra et al. | |
| 8,067,360 B2 | 11/2011 | Knopf et al. | |
| 8,110,355 B2 | 2/2012 | Atwood et al. | |
| 8,124,830 B2 | 2/2012 | Lee et al. | |
| 8,128,933 B2 | 3/2012 | Knopf et al. | |

(Continued)

FOREIGN PATENT DOCUMENTS

EP    1174149 A1    1/2002
EP    1 362 062 A1   11/2003

(Continued)

OTHER PUBLICATIONS

Cannon and Nedergaard, "Neither fat nor flesh," Nature, vol. 454(7207): 947-948 (2008).

Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).

(Continued)

*Primary Examiner* — Elizabeth C Kemmerer

(74) *Attorney, Agent, or Firm* — Ropes & Gray LLP

(57) ABSTRACT

The disclosure provides, among other aspects, neutralizing antibodies and portions thereof that bind to ActRIIA and uses for same.

12 Claims, 17 Drawing Sheets

(12 of 17 Drawing Sheet(s) Filed in Color)

(56) References Cited

U.S. PATENT DOCUMENTS

| | | |
|---|---|---|
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,236 B2 | 10/2012 | Lin et al. |
| 8,293,881 B2 | 10/2012 | Seehra et al. |
| 8,309,082 B2 | 11/2012 | Han et al. |
| 8,343,933 B2 | 1/2013 | Knopf et al. |
| 8,388,968 B2 | 3/2013 | Berger et al. |
| 8,410,043 B2 | 4/2013 | Sun et al. |
| 8,435,948 B2 | 5/2013 | Zaidi et al. |
| 8,501,678 B2 | 8/2013 | Sun et al. |
| 8,629,109 B2 | 1/2014 | Knopf et al. |
| 8,637,023 B2 | 1/2014 | Lin et al. |
| 8,703,694 B2 | 4/2014 | Knopf et al. |
| 8,703,927 B2 | 4/2014 | Seehra et al. |
| 8,716,459 B2 | 5/2014 | Sun et al. |
| 8,753,627 B2 | 6/2014 | Han et al. |
| 8,765,663 B2 | 7/2014 | Seehra et al. |
| 8,822,411 B2 | 9/2014 | Lee et al. |
| 8,865,168 B2 | 10/2014 | Lin et al. |
| 8,895,016 B2 | 11/2014 | Sherman et al. |
| 8,987,203 B2 | 3/2015 | Van Leeuwen et al. |
| 8,999,917 B2 | 4/2015 | Sun et al. |
| 2001/0039036 A1 | 11/2001 | Mathews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2003/0224501 A1 | 12/2003 | Young et al. |
| 2004/0033511 A1 | 2/2004 | Pfizenmaier et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0210657 A1 | 9/2006 | Chou |
| 2007/0048830 A1 | 3/2007 | Gilbert et al. |
| 2007/0117130 A1 | 5/2007 | Han et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2008/0261879 A1 | 10/2008 | Melton et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2009/0202471 A1 | 8/2009 | Khetani et al. |
| 2009/0226460 A1 | 9/2009 | Phillips et al. |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0113327 A1 | 5/2010 | Van Leeuwen et al. |
| 2010/0125099 A1 | 5/2010 | Hoen et al. |
| 2010/0183624 A1 | 7/2010 | Seehra et al. |
| 2010/0272734 A1 | 10/2010 | Berger et al. |
| 2010/0279409 A1 | 11/2010 | Robson et al. |
| 2010/0316644 A1 | 12/2010 | Seehra et al. |
| 2011/0038831 A1 | 2/2011 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0286998 A1 | 11/2011 | Gregory et al. |
| 2011/0293526 A1 | 12/2011 | Plikus et al. |
| 2012/0003218 A1 | 1/2012 | Sherman et al. |
| 2012/0015877 A1 | 1/2012 | Seehra et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2012/0232021 A1 | 9/2012 | Martini et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0108650 A1 | 5/2013 | Kumar et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0225484 A1 | 8/2013 | Sun et al. |
| 2013/0243743 A1 | 9/2013 | Seehra et al. |
| 2013/0244324 A1 | 9/2013 | Seehra et al. |
| 2013/0287765 A1 | 10/2013 | Zaidi et al. |
| 2013/0303068 A1 | 11/2013 | Hall et al. |
| 2013/0344091 A1 | 12/2013 | Berger et al. |
| 2014/0056902 A1 | 2/2014 | Shimizu et al. |
| 2014/0079700 A1 | 3/2014 | Knopf et al. |
| 2014/0194355 A1 | 7/2014 | Sun et al. |
| 2014/0220033 A1 | 8/2014 | Han et al. |
| 2014/0348827 A1 | 11/2014 | Sun et al. |
| 2015/0072927 A1 | 3/2015 | Lin et al. |
| 2015/0086556 A1 | 3/2015 | Han et al. |
| 2015/0111248 A1 | 4/2015 | Bancel et al. |
| 2015/0139983 A1 | 5/2015 | Karni et al. |
| 2015/0231206 A1 | 8/2015 | Sun et al. |
| 2015/0258120 A1 | 9/2015 | Zarnitsyn et al. |
| 2015/0266950 A1 | 9/2015 | Sung et al. |
| 2015/0276766 A1 | 10/2015 | Sung et al. |
| 2015/0283209 A1 | 10/2015 | Sung et al. |
| 2015/0328249 A1 | 11/2015 | Gonzalez-Cadavid et al. |

FOREIGN PATENT DOCUMENTS

| | | |
|---|---|---|
| EP | 1 416 273 A1 | 5/2004 |
| JP | 2007-099764 | 4/2007 |
| WO | WO-92/04913 A1 | 4/1992 |
| WO | WO-92/20793 A1 | 11/1992 |
| WO | WO 93/00432 A1 | 1/1993 |
| WO | WO-94/15965 A1 | 7/1994 |
| WO | WO-94/26893 A1 | 11/1994 |
| WO | WO-95/10611 A1 | 4/1995 |
| WO | WO-95/29685 A1 | 11/1995 |
| WO | WO-97/23613 A2 | 7/1997 |
| WO | WO 98/18926 A1 | 5/1998 |
| WO | WO-99/06559 A1 | 2/1999 |
| WO | WO-00/18932 A2 | 4/2000 |
| WO | WO 00/25807 A1 | 5/2000 |
| WO | WO-00/43781 A2 | 7/2000 |
| WO | WO-0062809 A1 | 10/2000 |
| WO | WO-01/36001 A2 | 5/2001 |
| WO | WO 01/43763 A1 | 6/2001 |
| WO | WO-02/10214 A2 | 2/2002 |
| WO | WO 02/22680 A2 | 3/2002 |
| WO | WO 02/36152 | 5/2002 |
| WO | WO 02/40501 A2 | 5/2002 |
| WO | WO-02/43759 A2 | 6/2002 |
| WO | WO 02/074340 A1 | 9/2002 |

(56) References Cited

FOREIGN PATENT DOCUMENTS

| WO | WO-02/085306 A2 | 10/2002 |
|---|---|---|
| WO | WO-02/094852 A2 | 11/2002 |
| WO | WO-03/006057 A1 | 1/2003 |
| WO | WO-03/053219 A2 | 7/2003 |
| WO | WO-03/072808 A1 | 9/2003 |
| WO | WO 03/087162 A2 | 10/2003 |
| WO | WO-2004/016639 | 2/2004 |
| WO | WO-2004/039948 | 5/2004 |
| WO | WO 2004/069237 A1 | 8/2004 |
| WO | WO 2004/086953 | 10/2004 |
| WO | WO 2004/092199 A2 | 10/2004 |
| WO | WO-2004/108157 A2 | 12/2004 |
| WO | WO-2005/003158 A2 | 1/2005 |
| WO | WO-2005/009460 A2 | 2/2005 |
| WO | WO-2005/014650 A2 | 2/2005 |
| WO | WO-2005/028517 A2 | 3/2005 |
| WO | WO-2005/053795 A2 | 6/2005 |
| WO | WO-2005/070967 A2 | 8/2005 |
| WO | WO-2005/094871 A2 | 10/2005 |
| WO | WO-2005/097825 A2 | 10/2005 |
| WO | WO-2005/113590 A2 | 12/2005 |
| WO | WO-2006/002387 A2 | 1/2006 |
| WO | WO-2006/012627 A2 | 2/2006 |
| WO | WO-2006/020884 A2 | 2/2006 |
| WO | WO-2006/115274 A1 | 2/2006 |
| WO | WO-2006/039400 A2 | 4/2006 |
| WO | WO-2006/083183 A1 | 8/2006 |
| WO | WO-2006/088972 | 8/2006 |
| WO | WO-2007024715 A2 | 3/2007 |
| WO | WO-2007/038703 A2 | 4/2007 |
| WO | WO-2007/053775 A1 | 5/2007 |
| WO | WO-2007/062188 | 5/2007 |
| WO | WO-2007/067616 A2 | 6/2007 |
| WO | WO 2007/071023 A1 | 6/2007 |
| WO | WO 2007/075702 A2 | 7/2007 |
| WO | WO-2007/076127 A2 | 7/2007 |
| WO | WO 2007/087505 A2 | 8/2007 |
| WO | WO 2007/101060 A2 | 9/2007 |
| WO | WO-2008/015383 A2 | 2/2008 |
| WO | WO-2008/031061 | 3/2008 |
| WO | WO-2008/060139 A1 | 5/2008 |
| WO | WO-2008/072723 A1 | 6/2008 |
| WO | WO-2008/073292 A2 | 6/2008 |
| WO | WO-2008/076437 A2 | 6/2008 |
| WO | WO-2008/094708 A2 | 8/2008 |
| WO | WO-2008/097541 A2 | 8/2008 |
| WO | WO-2008/100384 A2 | 8/2008 |
| WO | WO-2008/109167 A2 | 9/2008 |
| WO | WO-2008/151078 A8 | 12/2008 |
| WO | WO-2009/009059 A1 | 1/2009 |
| WO | WO-2009/019504 A1 | 2/2009 |
| WO | WO-2009/019505 A2 | 2/2009 |
| WO | WO 2009/021747 A2 | 2/2009 |
| WO | WO-2009/025651 A1 | 2/2009 |
| WO | WO-2009/070243 A2 | 6/2009 |
| WO | WO 2009/114180 A1 | 9/2009 |
| WO | WO-2009/137075 A1 | 11/2009 |
| WO | WO-2009/137613 A2 | 11/2009 |
| WO | WO-2009/158015 A2 | 12/2009 |
| WO | WO-2009/158025 A2 | 12/2009 |
| WO | WO-2009/158033 A2 | 12/2009 |
| WO | WO-2010/019261 A1 | 2/2010 |
| WO | WO-2010/083034 A1 | 7/2010 |
| WO | WO-2010125003 A1 | 11/2010 |
| WO | WO-2010144452 A1 | 12/2010 |
| WO | WO-2010151426 A1 | 12/2010 |
| WO | WO-2011020045 A1 | 2/2011 |
| WO | WO-2011/031901 A1 | 3/2011 |
| WO | WO-2012/027065 A2 | 3/2012 |
| WO | WO-2013006437 A1 | 1/2013 |
| WO | WO-2013/059347 A1 | 4/2013 |
| WO | WO-2013/063536 A1 | 5/2013 |
| WO | WO-2014/066487 A2 | 5/2014 |
| WO | WO-2014064292 A1 | 5/2014 |
| WO | WO-2014152940 A1 | 9/2014 |
| WO | WO-2015017576 A1 | 2/2015 |
| WO | WO-2015022658 A2 | 2/2015 |
| WO | WO-2015089575 A1 | 6/2015 |
| WO | WO-2015108972 A1 | 7/2015 |
| WO | WO-2015111008 A2 | 7/2015 |
| WO | WO-2015152183 A1 | 10/2015 |
| WO | WO-2015162590 A1 | 10/2015 |
| WO | WO-2015192127 A2 | 12/2015 |

OTHER PUBLICATIONS

Crisan et al., "A Reservoir of Brown Adipocyte Progenitors in Human Skeletal Muscle," Stem Cells, vol. 26(9): 2425-2433 (2008).

Donaldson et al., GenBank: BAA06548.1: activin typeII A receptor precursor [Homo sapiens] (1992).

Dussiot et al., "An activin receptor IIA ligand trap corrects ineffective erythropoiesis in B-thalassemia," Nature Medicine, vol. 20: 398-407 (2014).

Ear et al., "RAP-011 Efficiently Rescues Erthropoiesis in Zebrafish Models of Diamond Blackfan Anemia," 55 ASH Annual Meeting and Exposition. Abstract #3702 (2013).

Farmer, Stephen R., "Brown Fat and Skeletal Muscle: Unlikely Cousins?," Cell, vol. 134(5): 726-727 (2008).

Ferguson et al., "The role of effectors of the activin signalling pathway, activin receptors IIA and IIB, and Smad2, in patterning of tooth development," Development, vol. 128: 4605-4613 (2001).

Frankel et al., "Characterization of diphtheria fusion proteins targeted to the human interleukin-3 receptor," Protein Engineering, vol. 13(8): 575-581 (2000).

Kanemitsu, Fusae, "Clinical application of subforms of creatine kinase MM and macro creatine kinases," Journal of Chromatography, vol. 526: 423-438 (1990).

Lazar, E., et al., "Transforming Growth Factor α: Mutation of Aspartic Acid 47 and Leucine 48 Results in Different Biological Activities," Molecular and Cellular Biology, 8(3):1247-1252 (1988).

McPherron and Lee, "Suppression of body fat accumulation in myostatin-deficient mice," The Journal of Clinical Investigation, vol. 109(5): 595-601 (2002).

Moore et al., "Molecular Basis of Bone Morphogenetic Protein-15 Signaling in Granulosa Cells," The Journal of Biological Chemistry, vol. 278(1): 304-310 (2003).

Morrison et al., "A soluble activin type IIB receptor improves function in a mouse model of amyotrophic lateral sclerosis," Experimental Neurology vol. 217: 258-268 (2009).

The website downloaded Oct. 28, 2014 from the Multiple Myeloma Research Foundation, themmrf.org/multiple-myeloma/symptoms/bone-lesions/, 2 pages total.

NIH website downloaded May 28, 2014 from: web.archive.org/web/20030409091558/http://www.cc.nih .gov/ccc/patient_education/pepubs/subq.pdf; Patient Information Publications: Giving a Subcutaneous Injection ( 6 pages total).

Pakula and Sauer, "Genetic analysis of protein stability and function," Annu. Rev. Genet., vol. 23: 289-310 (1989).

Seale et al., "PRDM16 controls a brown fat/skeletal muscle switch," Nature, vol. 454(7207): 961-967 (2008).

Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).

US Biological Technical Data Sheet for A0856-10A, accessed on Feb. 20, 2013.

Abaza, M.S.I., et al., "Effects of Amino acid Substitutions Outside an Antigenic Site," J. Protein Chem., 11(5):433-444 (1992).

Abbiotec: ACTR-IIA Antibody: Catalog No. 251303 (http://www.abbiotec.com) Jun. 3, 2010.

Acceleron Pharma Presents Positive Phase 1 Results Demonstrating ACE-011 Increases Markers of Bone Formation, Acceleron Pharma, pp. 1-2, <www.acceleronpharma.com/contents/news/press-releases/detail.jsp/q/news-id/47> Downloaded from the Internet on Feb. 17, 2009.

Acta Cryst.,"The CCP4 suite: programs for protein crystallography: Collaborative Computational Project, No. 4," D50: 760-763 (1994).

(56) References Cited

OTHER PUBLICATIONS

Akel et al, Neutralization of Autocrine Transforming Growth Factor -β in Human Cord Blood CD34+CD38−Lin− Cells Promotes Stem-Cell-Factor-Mediated Erythropoietin-Independent Early Erythroid Progenitor Development and Reduces Terminal Differentiation. Stem Cells, 21:557-567 (2003).
Akpan, I., et al., "The effects of a soluble activin type IIB receptor on obesity and insulin sensitivity," International Journal of Obesity, 33(11):1265-1273 (2009).
Allendorph, G.P., et al., "Structure of the ternary signaling complex of a TGF-β superfamily member," PNAS, 103(20):7643-7648 (2006).
Anonymous "Learning about Thalassemia" <http://www.genome.gov/10001221> Accessed on Internet Jul. 9, 2013.
Anonymous "Iron and Thalassemia," Accessed on the Internet Apr. 3, 2014 at <sickle.bwh.harvard.edu/thaliron.html>. Published Aug. 25, 1997.
Anti-ActRIIA Antibodies: Commercial Monoclonal Antibodies Against Human ActRIIA (2010).
"Anti-human Activin RIIA Antibody," R&D Systems, Catalog No. AF340 (Feb. 14, 2006).
Antibodies for ACVR2A: <http://www.genecards.org/cgi-bin/card-disp.pl?gene=Acvr2a> (Jun. 8, 2010).
Attie et al., "A Single Ascending-Dose Study of Muscle Regulator Ace-031 in Healthy volunteers," Muscle & Nerve, pp. 1-8 (2012).
Banks, G.B., et al., "The Value of Mammalian Models for Duchenne Muscular Dystrophy in Developing Therapeutic Strategies," Current Topics in Developmental Biology, 84:431-453 (2008).
Benny Klimek, Margaret E., et al., "Acute inhibition of myostatin-family proteins preserves skeletal muscle in mouse models of cancer cachexia," Biochemical and Biophysical Research Communications, 391:1548-1554 (2010).
Berenson, J.R., "Multiple Myeloma," Multiple Myeloma: Plasma Cell Disorders: Merck Manual Professional, pp. 1-5, Jul. 2008.
Bhatia et al., Protein Glycosylation: Implications for In Vivo Functions and Therapeutic Applications. Advances in Biochemical Engineering/Biotechnology, vol. 64: 155-201 (1998).
Binkert, et al., "Cloning, sequence analysis and expression of a cDNA encoding a novel insulin-like growth factor binding protein (IGFBP-2)," The EMBO Journal, 8(9):2497-2502 (1989).
Bodey, B., et al., "Failure of Cancer Vaccines: The Significant Limitations of this Approach to Immunotherapy," Anticancer Research, 20:2665-2676 (2000).
Bogdanovich, S., et al., "Functional improvement of dystrophic muscle by myostatin blockade," Nature, 420:418-421 (2002).
Bork, "Powers and Pitfalls in Sequence Analysis: The 70% Hurdle," Genome Research, 10:398-400 (2000).
Bowie, J.U., et al., "Deciphering the Message in Protein Sequences: Tolerance to Amino Acid Substitutions," Science, 257:1306-1310 (1990).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., Activin A mediates growth inhibition and cell cycle arrest through Smads in human breast cancer cells. Cancer Research, 65(17):7968-7975; Abstract (2005).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).
Cadena, S.M., et al., "Administration of a Soluble Activin Type IIB Receptor Promotes Skeletal Muscle Growth Independent of Fiber Type," Journal of Applied Physiology, 109:635-642 (2010).
Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2010).
Centrella et al., "Activin-A Binding and Biochemical Effects in Osteoblast-Enriched Cultures from Fetal-Rat Parietal Bone," Molecular and Cellular Biology, 11(1):250-58 (1991).
Chamberlain, R.S., et al., "Innovations and strategies for the development of anticancer vaccines," Expert Opinion on Pharmacotherapy, 1(4):603-614 (2000).
Chamow, S.M., and Ashkenazi, A., "Immunoadhesins: Principles and Applications," TIBTECH, 14: 52-60 (1996).
Chang, Sam S., "Exploring the Effects of Luteinizing Hormone-Releasing Hormone Agonist Therapy on Bone Health: Implications in the Management of Prostate Cancer," Urology, vol. 52: 29-35 (2003).
Chapman, B., et al., "Effect of intron A from human cytomegalovirus (Towne) immediate-early gene on heterologous expression in mammalian cells," Nucleic Acids Research, 19(14):3979-3986 (1991).
Chardès et al., "Efficient amplification and direct sequencing of mouse variable regions from any immunoglobulin gene family," FEBS Lett. vol. 452(3): 386-394 (1999).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Chen, Y.G., et al. "Regulation of Cell Proliferation, Apoptosis, and Carcinogenesis by Activin," Exp. Biol. Med., 227(2):75-87 (2002).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Cirillo et al., "Hematocrit, blood pressure, and hypertension. The Gubbio Population Study," Hypertension, 20(3):319-326 (1992).
Coerver, et al., "Activin Signaling through Activin Receptor Type II Causes the Cachexia-Like Symptoms in Inhibin-Deficent Mice," 10(5):534-543 (1996).
Collins, C.D., "Multidisciplinary Symposium: Haematological Malignancies," Cancer Imaging 5:S119-S126 (2005).
Colman, P.M., et al., "Effects of amino acid sequence changes on antibody-antigen interactions," Research of Immunology, 145(1):33-36 (1994).
Daluiski et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028; Database accession No. GSP:ADY85028; abstract, sequence (2005).
Deal, C., "Potential New Drug Targets for Osteoporosis," Nature Clinical Practice, 5(1):20-27 (2009).
Deconinck, N., et al., "Pathophysiology of Duchenne Muscular Dystrophy: Current Hypotheses," Pediatr. Neurol., 36:1-7 (2007).
del Re et al., "Reconstitution and Analysis of Soluble Inhibin and Activin Receptor Complexes in a Cell-free System," The Journal of Biological Chemistry, 279(51):53126-53135 (2004).
Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).
Donald et al., "SDR: a database of predicted specificity-determining residues in proteins," Nucleic Acids Research, vol. 37: D191-D194 (2009).

(56) References Cited

OTHER PUBLICATIONS

Donaldson, et al., "Activin and inhibin binding to the soluble extracellular domain of activin receptor II", Endocrinology 140(4):1760-1766 (1999).
Donaldson, et al., "Molecular Cloning and Binding Properties of the Human Type II Activin Receptor", Biochemical and Biophysical Research Communications, 184(1):310-316 (1992).
Eijken, M., "The Activin A-Follistatin System: Potent Regulator of Human Extracellular Matrix Mineralization," The FASEB Journal, 21:2949-2960 (2007).
Elliot et al., "Enhancement of therapeutic protein in vivo activities through glycoengineering," Nature Biotechnology, vol. 21: 414-421 (2003).
Fafioffe, et al.,"Activin and inhibin receptor gene expression in the ewe pituitary throughout the oestrous cycle," Journal of Endocrinology, 182:55-68 (2004).
Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).
Fan, et al., "Preclinical evaluation of Hematide, a novel erythropoiesis stimulating agent, for the treatment of anemia," Experimental Hematology 34, pp. 1303-1311 (2006).
Frigon, N.L., et al, "Regulation of Globin Gene Expression in Human K562 Cells by Recombinant Activin A," Blood, 79(3):765-772 (1992).
Foucar, K., Myelodysplastic/Myeloproliferative Neoplasms, Am J Clin Pathol, vol. 132: 281-289 (2009).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gilbert, R., et al., "Prolonged dystrophin expression and functional correction of mdx mouse muscle following gene transfer with a helper-dependent (gutted) adenovirencoding murine dystrophin," Human Molecular Genetics, 12(11)1287-1299 (2003).
Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).
Gonzalez-Cadavid, N.F., et al., "Organization of the human myostatin gene and expression in healthy men and HIV-infected men with muscle wasting," PNAS, 95:14938-14943 (1998).
Gray, et al., "Identification of a binding site on the type II activin receptor for activin and inhibin", Journal of Biological Chemistry, 275(5):3206-3212(2000).
Greenspan, N.S., et al., "Defining epitopes: Its not as easy as it seems," Nature Biotechnology, 17:936-937 (1999).

Greenwald, et al., "Characterization of the Extracellular Ligand-Binding Domain of the Type II Activin Receptor," Biochemistry, 37(47):16711-16718 (1998).
Greenwald, et al., "The BMP7/ActRII Extracellular Domain Complex Provides New Insights into the Cooperative Nature of Receptor Assembly," Molecular Cell, 11:605-617 (2003).
Greenwald, J., et al., "Three-finger toxin fold for the extracellular ligand-binding domain of the type II activin receptor serine kinase," Nature Structural Biology, 6(1):18-22 (1999).
Gregoriadis, G., et al., "Polysialic acids: potential in drug delivery," FEBS, 315(3):271-276 (1993).
Guo, et al., Protein Tolerance to Random Amino Acid Change. Proc. Natl. Acad. Sci. USA, 101(25):9205-9210 (Jun., 22, 2004). Epub Jun. 14, 2004.
Gupta, V. et al., "Transforming Growth Factor-b Superfamily: Evaluation as Breast Cancer Biomarkers and Preventive Agents," Current Cancer Drug Targets, 4:165-182 (2004).
Gura, T., "Cancer Models: Systems for Identifying New Drugs Are Often Faulty," Science, 278(5340):1041-1042 (1997).
Haidar et al., "Paraspinal extramedullary hematopoiesis in patients with thalassemia intermedia," Eur Spine J., vol. 19: 871-878 (2010).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, M.W., et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, C.A., et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," TRENDS in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Herbert, W.J., et al., The Dictionary of Immunology, Academic Press, 3rd Edition, London, pp. 58-59 (1985).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Holm et al., "Functional mapping and single chain construction of the anti-cytokeratin 8 monoclonal antibody TS1," ScienceDirect; Molecular Immunology, vol. 44(6): 1075-1084 (2007).
Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).
"Human Activin RIIA Antibody," R&D Systems, Tools for Cell Biology Research, Catalog No. MAB340 (May 18, 2010).
Ikenoue et al., "Inhibitory Effects of Activin-A on Osteoblast Differentiation During Cultures of Fetal Rat Calvarial Cells," Journal of Cellular Biochemistry, 75:206-214 (1999).
"The Illustrated Guide to Bone Marrow Diagnosis Second Edition," Ed. by G. Kumar. Originally published 2003.
International Search Report, PCT/US2011/059818, dated Mar. 14, 2012.
Ito et al., "Presence of activin signal transduction in normal ovarian cells and epithelial ovarian carcinoma," British Journal of Cancer, vol. 82(8): 1415-1420 (2000).

(56) References Cited

OTHER PUBLICATIONS

Kaiser, J., "First Pass at Cancer Genome Reveals Complex Landscape," Science, 313:1370 (2006).
Kaspar, B.K., et al., "Retrograde Viral Delivery of IGF-1 Prolongs Survival in a Mouse ALS Model," Science, 301:839-842 (2003).
Kim, et al., "Type IIa IgG-Fc Fusion Protein, Increases Hemoglobin and Hematocrit Levels in Postmenopausal Healthy Women," Blood, 112(11):1316 (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krag, T.O.B., et al., "Heregulin ameliorates the dystrophic phenotype in mdx mice," PNAS, 101(38):13856-13860 (2004).
Krneta, J., et al., "Dissociation of Angiogenesis and Tumorigenesis in Follistatin- and Activin-Expressing Tumors," Cancer Research, 66(11):5686-5695 (2006).
Krystal et al., Transforming Growth Factor β1 Is an Inducer of Erythroid Differentiation. J. Exp. Med. vol. 180 pp. 851-860 (1994).
Kubanek, B., "Introduction: The Role of the Microenvironment and Cytokines on the Modulation of Erythropoiesis," Annals New York Academy of Sciences, pp. 257-258 (1994).
Kumar, T.R., et al., "Regulation of FSHβ and GnRH Receptor Gene Expression in Activin Receptor II Knockout Male Mice," Mol. Cell. Endocrinol., 212(1-2):19-27 (2003).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-based strategies for drug design and discovery," Science, 257(5073):1078-1082 (1992).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun, S., et al., "A Soluble Activin Receptor Type IIA Fusion Protein (ACE-011) Increases Bone Mass via a Dual Anabolic-Antiresorptive Effect in Cynomolgus Monkeys," Bone, 46:1082-1088 (2010).
Lu, S., et al., "Simian Immunodeficiency Virus DNA Vaccine Trial in Macaques," Journal of Virology, 70(6):3978-3991 (1996).
Ludlow, H., et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).
Maguer-Satta, V., et al, "Regulation of human erythropoiesis by activin A, BMP2, and BMP4, members of the TGFβ family," Experimental Cell Research, 282:110-120 (2003).
Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).
Mathews, L.S., et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McCarthy et al., Monoclonal antibodies that recognize the type-2 activin receptor, ACTR2, Hybridoma, vol. 13(3): 199-203 (1994) (abstract).
McNally, E.M., "Powerful Genes—Myostatin Regulation of Human Muscle Mass," N. Engl. J. Med., 350(26):2642-2644 (2004).
McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).
McPherron, A.C., et al., "Regulation of Skeletal Muscle Mass in Mice by a Bew TGF-b Superfamily Member," Nature, 387:83-90 (1997).
McPherson, S.J., et al., "Growth inhibitory response to activin A and B by human prostate tumour cell lines LNCaP and DU1465", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Mickle, et al., "Genotype-Phenotype Relationships in Cystic Fibrosis," Med. Clin. North Am., 84(3):597-607 (2000).
Miller et al., Ligand binding to proteins: the binding landscape model. Protein Sci., 6(10):2166-79 (1997).
Miura, P., et al., "Utrophin upregulation for treating Duchenne or Becker muscular dystrophy: how close are we?," Trends in Molecular Medicine, 12(3):122-129 (2006).
"Monoclonal Anti-human Activin RII Antibody," R&D Systems, Catalog No. MAB3391 (Feb. 19, 2009).
Mosekilde, L., et al., "Emerging Anabolic Treatments in Osteoporosis," Current Drug Safety, 6:62-74 (2011).

(56) References Cited

OTHER PUBLICATIONS

Murase et al., "Possible Involvement of Protein Kinases and Smad2 Signaling Pathways on Osteoclast Differentiation Enhanced by Activin A," Journal of Cellular Physiology, 188:236-242 (2001).
Murata, T., et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Nemeth, E., "Hepcidin in β-thalassemia," Annals of the New York Academy of Sciences, vol. 1202: 31-35. Published Aug. 2, 2010.
Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9: 133-139 (1995).
Patel, K., et al., "The function of Myostatin and strategies of Myostatin blockade—new hope for therapies aimed at promoting growth of skeletal muscle," Neuromuscular Disorders, 15:117-126 (2005).
Paul, William E., Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA Apr. 5-9, 2008 (Abstract).
Pearsall, et al., "A Soluble Activin Receptor Type IIA (ACTRIIA) Acts as a Novel Bone Anabolic Agent," The Official Journal of the European Calcified Tissue Society, 34th Europena Symposium on Calcified Tissues, May 2007.
Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall, R.S., et al., "A soluble activin Type IIA receptor induces bone formation and improves skeletal integrity", PNAS, vol. 105(19):7082-7087 (2008).
Perrien, D. S., et al., "Inhibin A Is an Endocrine Stimulator of Bone Mass and Strength," Endocrinology, 148(4):1675-1665 (2007).
Phillips, A.J., "The challenge of gene therapy and DNA delivery," J. Pharm. Pharmacology, 53:1169-1174 (2001).
Pirollo, K.F., et al., "Targeted Delivery of Small Interfering RNA: Approaching Effective Cancer Therapies," Cancer Res., 68(5):1247-1250 (2008).
Qi, et al., "Blockade of type β transforming growth factor signaling prevents liver fibrosis and dysfunction in the rat," PNAS, 96:2345-2349 (1999).
Raju, T.S., "Glycosylation in the Fc domain of IgG increases resistance to proteolytic cleavage by papain," Biochemical and Biophysical Research Communications, 341:797-803 (2006).
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIA/Fc Chimera," R&D Systems 340-R2 (Aug. 27, 2003).
"Recombinant Human Activin RIIB/Fc Chimera," R&D Systems 339-RB/CF (Aug. 27, 2003).
Reis, F.M., et al., "Activin, Inhibin and the Human Breast," Molecular and Cellular Edocrinology, 225:77-82 (2004).
Risbridger, G.P, et al., "Activins and Inhibins in Endocrine and Other Tumors," Endocrine Reviews, 22(6):836-858 (2001).
Robinson, G.W., et al., "Inhibins and Activins Regulate Mammary Epithelial Cell Differentiation Through Mesenchymal-epithelial Interactions," Development, 124:2701-2708 (1997).
Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).
Ruzek et al. Minimal Effects on Immune Parameters Following Chronic Anti-TGF-β Monoclonal Antibody Administration to Normal Mice. Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., The Measurement of Activin/EDF in Mouse Serum: Evidence for Extragonadal Production. Biochecmical and Biophysical Research Communications, 188(2):921-926 (1992).
Sakai, et al., "Osteogenic Activity of Activin in Young Normal Rats and Young Adult and Aged Rats after Ovariectomy," Bone 23:(Suppl.) 467 (1998).
Sako, D., et al., "Characterizationof the Ligand Binding Functionality of the Extracellular Domain of Activin Receptor Type IIB," The Journal of Biological Chemistry, 285(27):21037-21048 (2010).
Satoh, et al., "Hemodynamic changes by recombinant erythropoietin therapy in hemodialyzed patients," Hypertension, 15(3):262-266 (1990).
Schmelzer, C.H., et al., "Purification and Characterization of Recombinant Human Activin B," Biochimica et Biophysica Acta, 1039(2):135-141 (1990).
Schuelke, M., et al., "Myostatin Mutation Associated with Gross Muscle Hypertrophy in a Child," New England Journal of Medicine, 350(26):2682-2688 (2004).
Shao, L., et al., "Effect of Activin A on Globin Gene Expression in Purified Human Erythroid Progenitors," Blood, 79(3):773-781 (1992).
Shao, L., et al., "Efficient synthesis of globoside and isoglobside tetrasaccharides by using beta (1→3) N-acetylgalactosaminyltransferase/UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shav-Tal, Y., et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).

(56) References Cited

OTHER PUBLICATIONS

Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Smith, L. et al., "The analysis of doxorubicin resistance in human breast cancer cells using antibody microarrays," Mol. Cancer Therapy, vol. 5: 2115-2120 (2006).
Smith, L. et al., The Status, Quality, and Expansion of the NIH Full-Length cDNA Project: The Mammalian Gene Collection (MGC), Genome Res., vol. 14(10b),: 2127-2127 (2004).
Song, J., et al., "The Type II Activin Receptors Are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S49-S75 (2007).
Sun, et al., "FSH Directly Regulates Bone Mass," Cell, 125:247-260 (2006).
Supplementary European Search Report, EP 11 83 9434, dated Mar. 11, 2014.
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010.
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Tanno, T. and Miller, J.L., "Iron Loading and Overloading due to Ineffective Erythropoiesis," Advances in Hematology, Article ID 358283, Chapter 2 (Abstract) (2010).
Thompson, et al., "Structures of an ActRIIB: activin A complex reveal a novel binding mode for TGF-beta ligand: receptor interactions", EMBO 22(7):1555-1566 (2003).
Thompson, T.B., et al., "Beta A versus beta B: is it merely a matter of express?," Molecular and Cellular Endocrinology, 225:9-17 (2004).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tinsley, J., et al., "Expression of full-length utrophin prevents muscular dystrophy in *mdx* mice," Nature Medicine, 4(12):1441-1444 (1998).
Tisdale, M.J., "Cachexia in Cancer Patients," Nat. Rev. Cancer, 2:862-87 (2002).
Tokuriki, N., et al., "Stability effects of mutations and protein evolvability," Current Opinion in Structural Biology, 19:596-604 (2009).
Trivedi, R., et al., "Investigational Anabolic Therapies for Osteoporosis," Expert Opin. Investig. Drugs, 19(8):995-1005 (2010).
Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).

Tsuchida, et al., "Activin isoforms signal through type I receptor serine/threonine kinase ALK7," Molecular and Cellular Endocrinology, 220:59-65 (2004).
Tu, P., et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola, et al., "Adiponectin: A Link Between Excess Adiposity and Associated Comorbidities?", Journal of Molecular Medicine, 80(11):696-702 (2002).
US Biological, Activin Receptor Type IIA (RIIA) A0856-05E www.usbio.net/technicalsheet.php?item=A0856-05E dated Jun. 8, 2010.
Utzschneider, et al., The Role of Insulin Resistance in Nonalcoholoc Fatty Liver Disease, J. Clin. Endocrinol. Metab., 944212917_11(12):4753-4761 (Dec. 2006). Epub Sep. 12, 2006.
Vallet, S., et al., "Activin A promotes multiple myeloma-induced osteolysis and is a promising target for myeloma bone disease," PNAS, 107(11):5124-5129 (2010).
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Vidal, L., et al., "Making sense of antisense," European Journal of Cancer, 41:2812-2818 (2005).
Wagner, K.R., et al., "A Phase I/II trial of MYO-029 in Adult Subjects with Muscular Dystrophy," Ann. Neurol., 63:561-571 (2008).
Wagner, K.R., et al., "Loss of Myostatin Attenuates Severity of Muscular Dystrophy in *mdx* Mice," Ann. Neurol., 52:832-836 (2002).
Wagner, K.R., et al., "Muscle regeneration in the prolonged absence of myostatin," PNAS, 102(7):2519-2524 (2005).
Walsh, F. S, et al., "Myostatin: a modulator of skeletal-muscle stems cells," Biochemical Society Transactions, 33(Pt.6):1513-1517 (2005).
Wang, et al., A single amino acid determines lysophospholipid specificity of the S1P1 (EDG1) and LPA1 (EDG2) phospholipid growth factor receptors. JBC 276:49213-49220 (2001).
Wang, W., et al., "GDF-3 is an adipogenic cytokine under high fat dietary condition," Biochemical and Biophysical Research Comm., 321(4):1024-1031 (2004).
Ward, R., "An update on disordered iron metabolism and iron overload," Hematology, vol. 15(5): 311-317 (2010).
Weber, et al., A slient H-bond can by mutationally activated for high-affinity interaction of BMP-2 and activin type IIB receptor, BMC Structural Biology, 7(6):1-20 (2007).
Wells, J.A., "Additivity of Mutational Effects in Proteins," Biochemistry, 29(37):8509-8517 (1990).
Welt, et al., "Activin: an endocrine or panacrine agent?," European Journal of Endocrinology 139:469-471 (1998).
Wiater, et al., "Inhibin is an Antagonist of Bone Morphogenetic Protein Signaling," The Journal of Biological Chemistry, 278(10):7934-7941 (2003).
Wolfman, N.M., et al., "Activation of latent myostatin by the BMP-1/tolloid family of metalloproteinases," PNAS, 100(26):15842-15846 (2003).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated and original).
Yokota, T., et al., "Isolation and characterization of a mouse cDNA clone that expresses mast-cell growth-factor activity in monkey cells," Proc. Natl. Acad. Sci. USA, 81:1070-1074 (1984).

(56) References Cited

OTHER PUBLICATIONS

Yu et al., "Specific roles of activin/inhibin in human erythropoiesis in vitro." Annals New York Academy of Sciences, 20(10):1243-1246 (1991).
Yu, J., et al., "Importance of FSH-releasing protein and inhibin in erythrodifferentiation," Nature, 330:765-767 (1987).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhao, B., et al., "Transgenic expression of myostatin propeptide prevents diet-induced obesity and insulin resistance," Biochemical and Biophysical Research Communications, 337:248-255 (2005).
Zhang et al., Effects of Activin A on the Activities of the Mouse Peritoneal Macrophages, Cellular & Molecular Immunology, vol. 2(1): 63-67 ( 2005).
Datta-Mannan et al, Addendum to "An Engineered Human Follistatin Variant: Insights into the Pharmacokinetic and Pharmocodynamic Relationships of a Novel Molecule with Broad Therapeutic Potential," The Journal of Pharmacology and Experimental Therapeutics, 1 page (2013).
Keutmann et al, "The Role of Follistatin Domains in Follistatin Biological Action," Molecular Endocrinology 1:228-240 (2003).
Pennucci et al., "Multiplexed Evaluation of a Cell-Based Assay for the Detection of Antidrug Neutralilzing Antibodies to Panitumumab in Human Serum Using Automated Fluorescent Microscopy," Journal of Biomolecular Sceening 15:644-652 (2010).
R&D Systems Catalogue No. AF339 Datasheet: Human Activin RIIB Antibody [retrieved on Feb. 13, 2013] Retrieved from the Internet: http://www.rndsystems.com/pdf/af339.pdf.
R&D Systems, "Antibody Reference Guide and Catalog Instructions," [retrieved on Feb. 13, 2013]; http://web.archive.org/web/20090220022132/http://rndsystems.com/DAM_public/5658.pdf; published Mar. 14, 2009 as per the Wayback Engine. See, in particular: p. 3.
Sirskyj et al., Detection of Influenza A and B Neutralizing Antibodies in Vaccinated Ferrets and Macaques Using Specific Biotinstreptavidin Conjugated Antibodies, Journal of Virological Methods 163:459-464 (2010).
Winkler et al., "Sclerostin Inhibition of Wnt-3a-induced C3H10T1/2 Cell Differentiation Is Indirect and Mediated by Bone Morphogenetic Proteins," The Journal of Biological Chemistry 280(4):2498-2502 (2005).
Abrahams, B. and Ertel, S., 'Acceleron Pharma at Wells Fargo Healthcare Conference—Final', published on Jun. 17, 2014, Fair Disclosure Wire (Quarterly Earnings Reports), Accession No. 32U3101469591FDW.
Acceleron, 'Corporate Overview', considered published in Jul. 31, 2014, Retrieved on Aug. 20, 2015 from the Internet.
Acceleron, 'Review of the Data Presented at the European Hematology Association 19th Annual Meeting', considered published on Jun. 16, 2014; Retrieved on Aug. 20, 2015 from the Internet.
BIOSIS Accession No. 2015:276893 & Piga, A. et al., 'ACE-536 Increases Hemoglobin and Decreases Transfusion Burden and Serum Ferritin in Adults with Beta-Thalassemia: Preliminary Results from a Phase 2 Study,' Blood, vol. 124(21): p. 53 (2014).
Carrancio, S. et al. "An activin receptor IIA ligand trap promotes erythropoiesis resulting in a rapid induction of red blood cells and haemoglobin," British Journal of Haematology, vol. 165: 870-882 (2014).
Genbank NP_001607.1, Activin A Type II receptor precursor [*Homo sapiens*], http://www.ncbi.nlm.nih.gov/protein/4501897?sat=34&satkey=10571517 (Apr. 22, 2005); downloaded Nov. 11, 2015.
Kwiatkowski, J.L. et al., "Iron chelation therapy in sickle-cell disease and other transfusion-dependent anemias," Hematol Oncol Clin N Am., vol. 18: 1355-1377 (2004). (abstract).
MacLennan et al., "Multiple Myeloma," BMJ, vol. 308:1033-1036 (1994).
Marri et al, Human Biochemistry, Moscow, "Mir", vol. 1: 34-35 (1993).
Merck Manual. Iron-Utilization Anemias (Sideroblastic Anemias), pp. 1150-1151 (1992).
The Merck Manual of Diagnosis and Therapy, 17th Edition. Nyelodysplastic Syndrome, pp. 865 and 963-955 (1999).
Nolan, V.G., et al, 'Sickle Cell Leg Ulcers: Associations with Haemolysis and SNPs in Klotho, TEK and Genes of the TGF-β/BMP Pathway:-Sickle Cell Leg Ulcers, Genetics and Haemolysis', British Journal of Haematology, 133(5), pp. 570-578 (2006).
Pak et al., "Suppression of hepcidin during anemia requires erythropoietic activity," Blood, vol. 108(12): 3730-3735 (2006).
Paulson, Robert F., "Targeting a new regulator of erythropoiesis to alleviate anemia," Nature Medicine, News and Views, vol. 20(4) (2 pages) (2014).
Sun Shuhan et al., "Chromosome, Gene, and Disesase," Science Press (2009).
Suragani et al., "Transforming growth factor-β superfamily ligand trap ACE-536 corrects anemia by promoting late-stage erythropoiesis," Letters, Nature Medicine, Advance Online Publication (44 pages) (2014).
Ware, Russell E., "How I use hydroxyurea to treat young patients with sickle cell anemia," Blood, vol. 115(26): 5300-5311 (2010).
ACTR-II (149/1): sc-57022, Santa Cruz Biotechnology, Inc.: http://datasheets.scbt.com/sc-57022.pdf, Dated Jun. 3, 2010.
ACTR-II (H-65): sc-25451, Santa Cruz Biotechnology, Inc.: http://datasheets.scbt.com/sc-25451.pdf, dated Jun. 3, 2010.
ACTR-II (D-15): sc-5669, Santa Cruz Biotechnology, Inc.: http://datasheets.scbt.com/sc-5669.pdf, dated Jun. 3, 2010.
ACTR-IIA (A-24): sc-130679, Santa Cruz Biotechnology, Inc.: http://datasheets.scbt.com/sc-130679.pdf, dated Jun. 3, 2010.
ACTR-IIA (N-17): sc-5667, Santa Cruz Biotechnology, Inc.: http://datasheets.scbt.com/sc-5667.pdf, dated Jun. 3, 2010.
Al-Omari et al., "Castration induced changes in dog prostate gland associated with diminished activin and activin receptor expression," Life Sciences, vol. 77(22): 2752-2759 (2005).
Declerck et al., "Generation of Monoclonal Antibodies against Autologous Proteins in Gene-inactivated Mice," The Journal of Biological Chemistry, vol. 270(15): 8397-8400 (1995).

1   DVQLQESGPG LVKPSQSLSL TCSVTGYSIT SGYYWNWIRQ FPGNKLEWMG

51  YISYDGSNNY NPSLINRISI TRDTSKNQFF LKLNSVTTED TATYFCASYA

101 YRNDVRFAYW GQGTLVTVSA        (SEQ ID NO: 12)

FIGURE 1

1    DIQMTQTTSS LSASLGDRVT ISCRASQDIS NFLNWYQQKP DGTVKLLIYF

51   TSRLHSGVPS RFSGSGSGTD YSLTITNLEQ EDIATYFCQQ GNTLPWTFGG

101  GTKLEIK        (SEQ ID NO: 13)

FIGURE 2

```
                  E   V   K   L   (original)
                  D   V   Q   L   (final)
       1  gatgtacagcttcaggagtcaggacctggcctcgtgaaaccttctcagtc 51  tctgtctctcacctgctctgtcactggctactccatcaccagtggttatt 101  actggaactggatccggcagtttccaggaaacaaactggaatggatgggc 151  tacataagctacgacggcagcaataactacaacccatctctcataaatcg 201  aatctccatcactcgtgacacatctaagaaccagttttcctgaagttga 251  attctgtgactactgaagacacagctacatatttctgtgcaagttatgcc 301  tataggaacgacgtgaggtttgcttactggggccaagggactctggtcac 351  cgtctccgca       (SEQ ID NO: 14)
```

FIGURE 3

```
  1  gatatccagatgacacagactacatcctccctgtctgcctctctgggaga
 51  cagagtcaccatcagttgcagggcaagtcaggacattagcaattttttaa
101  actggtatcagcagaaaccagatggaactgttaaactcctgatctacttc
151  acatcaagattacactcaggagtcccatcaaggttcagtggcagtgggtc
201  tggaacagattattctctcaccattaccaacctggagcaagaagatattg
251  ccacttacttttgccaacagggtaatacgcttccgtggacgttcggtgga
301  ggcaccaagctcgagatcaaa      (SEQ ID NO: 15)
```

FIGURE 4

```
          *                           **    ****
  1   DVQLQESGPG LVKPSQSLSL TCSVTGYSIT SGYYWNWIRQ FPGNKLEWMG
                                 1         CDR-H1

*    *                                               *
 51YISYDGSNNY NPSLINRISI TRDTSKNQFF LKLNSVTTED TATYFCASYA
        CDR-H2                                            2

**** * **
101YRNDVRFAYW GQGTLVTVSA
       CDR-H3
```

FIGURE 5

```
              ***          ***         **  ****  **  **    *
  1 AILGRSETQE CLFFNANWEK DRTNQTGVEP CYGDKDKRRH CFATWKNISG

*****  ***
 51 SIEIVKQGCW LDDINCYDRT DCVEKKDSPE VYFCCCEGNM CNEKFSYFPE

101 MEVTQPTSNP VTPKPP     (SEQ ID NO: 16)
```

FIGURE 6

```
                                        *  *  **                              **
  1    DIQMTQTTSS LSASLGDRVT ISCRASQDIS NFLNWYQQKP DGTVKLLIYE
                             1    CDR-L1

*** *              *                              **** *
 51    TSRLHSGVPS RFSGSGSGTD YSLTITNLEQ EDIATYFCQQ GNTLPWTFGG
       CDR-L2                                    2    CDR-L3

101    GTKLEIK
```

FIGURE 7

```
                          *         *                    *      *  *  *
  1  AILGRSETQE  CLFFNANWEK  DRTNQTGVEP  CYGDKDKRRH  CEATWKNISG

* *      *   * * * * *           *        *  *  *  *
 51  SIEIVKQGCW  LDDINCYDRT  DCVEKKDSPE  VYFCCCEGNM  CNEKFSYFPE

101  MEVTQPTSNP  VTPKPP
```

FIGURE 8

ACTRIIA BINDING AGENTS AND USES THEREOF

RELATED APPLICATIONS

This application is a continuation of U.S. application Ser. No. 13/291,958, filed Nov. 8, 2011 (now abandoned), and claims the benefit of U.S. Provisional Application No. 61/411,396, filed Nov. 8, 2010. The specifications of each of the foregoing applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jan. 24, 2014, is named PHPH061102_Seq.txt and is 14,871 bytes in size.

BACKGROUND OF THE INVENTION

The activin receptor, type II A (ActRIIA or ACVR2A) is a high affinity receptor for the activin proteins as well as other members of the TGF-beta superfamily. ActRIIA is generally thought to transduce signals that lead to the phosphorylation of one or more SMAD transcription factors, particularly SMADs 1, 2, 3 and 5. ActRIIA has been implicated in the regulation of a wide range of biological processes, including bone formation, muscle formation, red blood cell formation, tumor growth, immune function and the production of reproductive hormones, such as FSH.

Follicle-stimulating hormone (FSH) is produced by the anterior pituitary gland and regulates gonadal function, including the generation and maturation of gametes. FSH secretion from the pituitary is regulated by gonadotropin-releasing hormone (GnRH) from the brain in concert with gonadal hormones and paracrine effectors originating in the pituitary. Activin was originally identified by its ability to increase FSH secretion from pituitary gonadotropes, and activin-mediated signaling, in part through activin receptor type IIA (ActRIIA), is now thought to promote FSH secretion through actions at multiple regulatory levels (Gregory et al., 2004, Semin Reprod Med 22:253-267).

FSH release is necessary for ovulation in females and for maturation of sperm in males. In females, FSH stimulates follicular granulosa cell proliferation in the ovary and impacts synthesis of estrogen, a hormone which is integral to follicular maturation and ovulation. In males, FSH is involved in the maturation of sperm cells. More specifically, FSH action in males is directed at the Sertoli cells, which are a recognized target of the hormone and which support the process of sperm maturation (spermatogenesis). FSH is also produced in the prostate, where it is an important mediator of cell growth.

Accordingly, inhibitors of FSH release are useful as contraceptive agents in both males and females.

In addition to the function in fertility, FSH also plays a role in several disease states. Increased levels of FSH receptor are associated with prostate cancer, with the highest levels associated with hormone-refractory prostate cancer. Prostate cancer is the most common cancer in American men, with more than 200,000 new cases diagnosed each year, and approximately 30,000 deaths due to prostate cancer are projected for 2010 (Jemal A. et al. Cancer statistics, 2010. CA Cancer J Clin 60:277-300, 2010). Approximately 40% of individuals treated with surgery or radiation will develop recurrent prostate cancer (Walsh P C, Retik A B, Vaughan E D, eds. Campbell's Urology. 7th ed. Philadelphia, Pa.: WB Saunders Company; 1998). The most common treatment for recurrent prostate cancer is the suppression of testicular testosterone production via orchiectomy, estrogen treatment, antiandrogen administration, and/or GnRH agonist/antagonist treatment. This usually results in remission for 2-3 years, after which time prostate cancer becomes "hormone refractory," meaning that it develops the ability to grow despite the reduction of blood androgen concentrations to castrate levels. Consequently, improved compositions and methods are needed for treating prostate cancer, in particular hormone-refractory prostate cancer.

Pituitary tumors (adenomas) are non-cancerous growths that typically affect different hormone-producing regions, depending on the specific location of the tumor. Pituitary tumors account for about 15% of intracranial tumors, and are associated with significant morbidity due to local compressive effects, hormonal hypersecretion, or treatment-associated endocrine deficiency (Heaney A. P., et al.: Molecular Pathogenesis of Pituitary Tumors. In: Oxford Textbook of Endocrinology, Wass J. A. H. and Shalet S. M., (Eds.), Oxford University Press, Oxford, 2002). The great majority of pituitary adenomas are benign and are relatively slow growing. Pituitary tumors may, however, lead to overproduction of one or more of the pituitary hormones. FSH-secreting pituitary tumors often lead to the development of multicystic ovaries and to elevated estradiol levels. In turn, increases in estradiol levels contribute to health risks including endometrial and prostate cancer. Consequently, improved compositions and methods are needed for treating symptoms associated with FSH-secreting pituitary tumors.

The FSH signaling pathway has been associated with tumor angiogenesis in a wide range of tumor types. Radu A, et al. N Engl J Med. 2010 Oct. 21; 363(17):1621-30. Accordingly, compounds that inhibit FSH secretion are useful in a variety of treatments.

The disclosure provides, in part, antagonists of ActRIIA that may be used to inhibit FSH production as well as other uses.

SUMMARY OF THE INVENTION

The disclosure provides, among other aspects, antibodies and fragments thereof that bind to ActRIIA and inhibit ActRIIA- or activin-mediated signaling. A variety of uses for such proteins are described herein. For example, the antibodies may be used to increase muscle mass or lean body mass in patients having diseases or conditions that are characterized by muscle loss or damage, to decrease FSH in patients in need thereof, to treat cachexia, particularly cancer cachexia, to decrease adiposity and thereby treat disorders such as obesity, and as part of assays to identify known and novel ActRIIA-binding agents.

The disclosure relates to binding agents, such as antibodies, that specifically bind to ActRIIA and, optionally, inhibit the binding of one or more ActRIIA ligand, such as activin A, activin B, GDF11, myostatin, BMP7 and/or other known ActRIIA ligands. The binding agents can be characterized by their ability to cross-block the binding of at least one antibody disclosed herein to ActRIIA and/or to be cross-blocked from binding ActRIIA by at least one of said antibodies. In certain embodiments, an anti-ActRIIA antibody or fragment thereof may inhibit ActRIIA-mediated signaling in a cell line in vitro. ActRIIA-mediated signaling may be measured, for example, by contacting a cell that expresses ActRIIA with an ActRIIA ligand (e.g., activin A, activin B, myostatin or GDF-11) in the presence of an anti-ActRIIA antibody. In certain embodiments, a binding agent such as a neutralizing antibody or fragment thereof may inhibit binding of ActRIIA to one or more ActRIIA ligands by simultaneously contacting the extracellular domain of ActRIIA at multiple residues important for ligand binding. In part, the disclosure relates to binding agents, such as antibodies and fragments thereof, that contact one or more amino acids in the extracellular domain of human ActRIIA, selected from a group consisting of: (a) a phenylalanine at position 13 of SEQ ID NO: 16, (b) a phenylalanine at position 14 of SEQ ID NO: 16, (c) an asparagine at position 15 of SEQ ID NO: 16, (d) an asparagine at position 17 of SEQ ID NO: 16, (e) an aspartate at position 21 of SEQ ID NO: 16, (f) an arginine at position 22 of SEQ ID NO: 16, (g) a threonine at position 23 of SEQ ID NO: 16, (h) a glutamate at position 29 of SEQ ID NO: 16, (i) a proline at position 30 of SEQ ID NO: 16, (j) a cysteine at position 31 of SEQ ID NO: 16, (k) a tyrosine at position 32 of SEQ ID NO: 16, (l) a glycine at position 33 of SEQ ID NO: 16, (m) an aspartate at position 34 of SEQ ID NO: 16, (n) an aspartate at position 36 of SEQ ID NO: 16, (o) a lysine at position 37 of SEQ ID NO: 16, (p) an arginine at position 39 of SEQ ID NO: 16, (q) a histidine at position 40 of SEQ ID NO: 16, (r) a phenylalanine at position 42 of SEQ ID NO: 16, (s) a threonine at position 44 of SEQ ID NO: 16, (t) a lysine at position 46 of SEQ ID NO: 16, (u) a valine at position 55 of SEQ ID NO: 16, (v) a lysine at position 56 of SEQ ID NO: 16, (w) a glutamine at position 57 of SEQ ID NO: 16, (x) a glycine at position 58 of SEQ ID NO: 16, (y.) a cysteine at position 59 of SEQ ID NO: 16, (z) a tryptophan at position 60 of SEQ ID NO: 16, (aa) a leucine at position 61 of SEQ ID NO: 16, (bb) an aspartate at position 62 of SEQ ID NO: 16, (cc) an aspartate at position 63 of SEQ ID NO: 16, (dd) an isoleucine at position 64 of SEQ ID NO: 16, (ee) an asparagine at position 65 of SEQ ID NO: 16, (ff) a cysteine at position 66 of SEQ ID NO: 16, (gg) a lysine at position 76 of SEQ ID NO: 16, (hh) a glutamate at position 80 of SEQ ID NO: 16, (ii) a valine at position 81 of SEQ ID NO: 16, (jj) a phenylalanine at position 83 of SEQ ID NO: 16, and (kk) a cysteine at position 85 of SEQ ID NO: 16.

Multiple residues in ActRIIA-binding antibodies, or fragments thereof, can be used to contact regions in the extracellular domain of ActRIIA for the purpose of neutralizing ActRIIA signaling. As illustrated herein, highly conserved residues in VH include two cysteines that can serve as reference points for denoting variable residues. In certain aspects, the disclosure relates to binding agents, such as antibodies and fragments thereof, that comprise one or more amino acids selected from a group of VH residues consisting of: (a) a valine at position −20 from $cysteine_1$ of SEQ ID NO: 12, (b) a glycine at position +4 from $cysteine_1$ of SEQ ID NO: 12, (c) a tyrosine at position +5 from $cysteine_1$ of SEQ ID NO: 12, (d) a serine at position +9 from $cysteine_1$ of SEQ ID NO: 12, (e) a glycine at position +10 from $cysteine_1$ of SEQ ID NO: 12, (f) a tyrosine at position +11 from $cysteine_1$ of SEQ ID NO: 12, (g) a tyrosine at position +12 from $cysteine_1$ of SEQ ID NO: 12, (h) a tyrosine at position +32 from $cysteine_1$ of SEQ ID NO: 12, (i) an asparagine at position +37 from $cysteine_1$ of SEQ ID NO: 12, (j) an alanine at position +4 from $cysteine_2$ of SEQ ID NO: 12, (k) a tyrosine at position +5 from $cysteine_2$ of SEQ ID NO: 12, (l) an arginine at position +6 from $cysteine_2$ of SEQ ID NO: 12, (m) an asparagine at position +7 from $cysteine_2$ of SEQ ID NO: 12, (n) an aspartate at position +8 from $cysteine_2$ of SEQ ID NO: 12, (o) an arginine at position +10 from $cysteine_2$ of SEQ ID NO: 12, (p) an alanine at position +12 from $cysteine_2$ of SEQ ID NO: 12, (q) a tyrosine at position +13 from $cysteine_2$ of SEQ ID NO: 12; and (r) a conservative substitution of any of the foregoing.

Highly conserved residues in VL also include two cysteines that can serve as reference points for denoting variable residues. In certain aspects, the disclosure relates to binding agents, such as antibodies and fragments thereof, that comprise one or more amino acids selected from a group of VL residues consisting of: (a) an aspartate at position +5 from $cysteine_1$ of SEQ ID NO: 13, (b) a serine at position +7 from $cysteine_1$ of SEQ ID NO: 13, (c) an asparagine at position +8 from $cysteine_1$ of SEQ ID NO: 13, (d) a phenylalanine at position +9 from $cysteine_1$ of SEQ ID NO: 13, (e) a tyrosine at position +26 from $cysteine_1$ of SEQ ID NO: 13, (f) a phenylalanine at position +27 from $cysteine_1$ of SEQ ID NO: 13, (g) a serine at position +29 from $cysteine_1$ of SEQ ID NO: 13, (h) an arginine at position +30 from $cysteine_1$ of SEQ ID NO: 13, (i) a leucine at position +31 from $cysteine_1$ of SEQ ID NO: 13, (j) a serine at position +33 from $cysteine_1$ of SEQ ID NO: 13, (k) a serine at position −21 from $cysteine_2$ of SEQ ID NO: 13, (l) a glycine at position +3 from $cysteine_2$ of SEQ ID NO: 13, (m) an asparagine at position +4 from $cysteine_2$ of SEQ ID NO: 13, (n) a threonine at position +5 from $cysteine_2$ of SEQ ID NO: 13, (o) a leucine at position +6 from $cysteine_2$ of SEQ ID NO: 13, (p) a tryptophan at position +8 from $cysteine_2$ of SEQ ID NO: 13, and (q) a conservative substitution of any of the foregoing.

Provided herein are binding agents, such as antibodies and fragments thereof, that bind specifically to ActRIIA and comprise, consist of, or consist essentially of, at least one CDR sequence selected from SEQ ID NOs: 4, 5, 6, 7, 8, and 9, and polypeptides that are at least 80%, 85%, 90%, 95% or 100% identical to any of the foregoing. Also provided herein are binding agents, such as antibodies and fragments thereof, that bind specifically to ActRIIA and comprise, consist of, or consist essentially of, at least two CDR sequences from SEQ ID NOs: 4, 5, 6, 7, 8, and 9, and polypeptides that are at least 80%, 85%, 90%, 95% or 100% identical to any of the foregoing. In another embodiment are provided binding agents, such as antibodies and fragments thereof, that bind specifically to ActRIIA and comprise, consist of, or consist essentially of, at least three CDR sequences from SEQ ID NOs: 4, 5, 6, 7, 8, and 9, and polypeptides that are at least 80%, 85%, 90%, 95% or 100% identical to any of the foregoing. Another embodiment provides binding agents, such as antibodies and fragments thereof, that bind specifically to ActRIIA and comprise, consist of, or consist essentially of, at least four CDR sequences from SEQ ID NOs: 4, 5, 6, 7, 8, and 9, and polypeptides that are at least 80%, 85%, 90%, 95% or 100% identical to any of the foregoing. Still another embodiment provides binding agents, such as antibodies and fragments thereof, that bind specifically to ActRIIA and comprise, consist of, or consist essentially of, at least five CDR sequences from SEQ ID NOs: 4, 5, 6, 7, 8, and 9, and polypeptides that are at least 80%, 85%, 90%, 95% or 100% identical to any of the foregoing. In yet another embodiment are provided binding agents, such as antibodies and fragments thereof, that bind specifically to ActRIIA and comprise, consist of, or consist essentially of, at least six CDR sequences from SEQ ID NOs: 4, 5, 6, 7, 8, and 9, and polypeptides that are at least 80%, 85%, 90%, 95% or 100% identical to any of the foregoing.

The disclosure further relates to binding agents, such as antibodies and fragments thereof, that comprise three CDRs, CDR-H1, CDR-H2, and CDR-H3, wherein CDR-H1 comprises a sequence that is at least 80%, 85%, 90%, 95% or 100% identical to SEQ ID NO: 4, CDR-H2 comprises a sequence that is at least 80%, 85%, 90%, 95% or 100% identical to SEQ ID NO: 5, and CDR-H3 comprises a sequence that is at least 80%, 85%, 90%, 95% or 100% identical to SEQ ID NO: 6.

In certain embodiments, the disclosure relates to binding agents, such as antibodies and fragments thereof, that comprise a heavy chain comprising a polypeptide having at least 80%, 85%, 90%, 95% or 100% identity to SEQ ID NO: 12. In another embodiment, the invention relates to binding agents, such as antibodies and fragments thereof, that comprise a light chain comprising a polypeptide having at least 80%, 85%, 90%, 95% or 100% identity to SEQ ID NO: 13. In still another embodiment, the invention relates to binding agents, such as antibodies and fragments thereof, that comprise both a heavy chain and a light chain, wherein the heavy chain comprises a polypeptide having at least 80%, 85%, 90%, 95% or 100% identity to SEQ ID NO: 12 and the light chain comprises a polypeptide having at least 80%, 85%, 90%, 95% or 100% identity to SEQ ID NO: 13.

In another embodiment, the disclosure relates to a method of generating an antibody capable of specifically binding to ActRIIA, comprising immunizing a viable, homozygous ActRIIA-deficient mouse with antigen polypeptide derived from ActRIIA.

The invention further relates to a method of treating a condition in a patient having undesired ActRIIA- or activin-mediated signaling, including but not limited to cancer, elevated FSH, and insufficient lean body mass, or obesity, the method comprising administering an effective amount of an ActRIIA binding agent, such as an antibody or fragment thereof.

In certain aspects, the disclosure relates to antibodies that can treat ActRIIA-associated conditions such as neuromuscular disorders (e.g., muscular dystrophy and muscle atrophy), congestive obstructive pulmonary disease or pulmonary emphysema (and associated muscle wasting), muscle wasting syndrome, sarcopenia, cachexia, adipose tissue disorders (e.g., obesity), type 2 diabetes, and bone degenerative disease (e.g., osteoporosis). The ActRIIA-binding agents of the present invention can be used to decrease FSH in prostate cancer, or increase muscle in cancer cachexia, in combination with conventional cancer therapies as described herein. Accordingly, antibodies and fragments thereof that bind ActRIIA may be used in combination therapies for the treatment, prevention, or management of prostate cancer or cancer cachexia in patients in need thereof. As shown in the Examples, an antibody that inhibits activin A and/or activin B binding to ActRIIA can be used in vivo to decrease FSH levels, increase muscle, decrease fat and ameliorate cachexia.

The invention also provides pharmaceutical compositions comprising the ActRIIA binding agent, such as an antibody or fragment thereof, in which there can be one or more of a pharmaceutically acceptable excipient, diluent, or carrier. As disclosed herein, the antibody or fragment thereof can be conjugated to at least one of Fc, polyethylene glycol, albumin, or transferrin.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

FIG. 1 depicts the amino acid sequence of the heavy chain variable region (VH) of Ab-14E1 (SEQ ID NO: 12). The two highlighted amino acids may be included to complete the J fragment (underlined).

FIG. 2 depicts the amino acid sequence of the light chain variable region (VL) of Ab-14E1 (SEQ ID NO: 13).

FIG. 3 depicts a nucleotide sequence encoding VH of Ab-14E1 (SEQ ID NO: 14). The six highlighted nucleotides may be included to complete the J fragment. Two alternative, active N-terminal sequences are shown as "original" (sequence EVKL, SEQ ID NO:17) and "final" (sequence DVQL, SEQ ID NO:18).

FIG. 4 depicts a nucleotide sequence encoding VL of Ab-14E1 (SEQ ID NO: 15).

FIG. 5 depicts the specificity-determining residues (SDRs, highlighted, with asterisks) in the 14E1 Fab VH sequence (SEQ ID NO: 12) that contact the human ActRIIA extracellular domain (ECD) upon high-affinity binding, as determined by x-ray crystallographic analysis. The two cysteines in VH are numbered, and CDR sequences are underlined.

FIG. 6 depicts the amino acid sequence of the human ActRIIA ECD (SEQ ID NO: 16) and identifies the residues (highlighted, with asterisks) contacted by 14E1 Fab VH upon high-affinity binding, as determined by crystallographic analysis.

FIG. 7 depicts the specificity-determining residues (SDRs, highlighted, with asterisks) in the 14E1 Fab VL sequence (SEQ ID NO: 13) that contact the human ActRIIA ECD upon high-affinity binding, as determined by crystallographic analysis. The two cysteines in VL are numbered, and CDR sequences are underlined.

FIG. 8 depicts the amino acid sequence of the human ActRIIA ECD (SEQ ID NO: 16) and identifies the residues (highlighted, with asterisks) contacted by 14E1 Fab VL upon high-affinity binding, as determined by crystallographic analysis.

Figure 13:
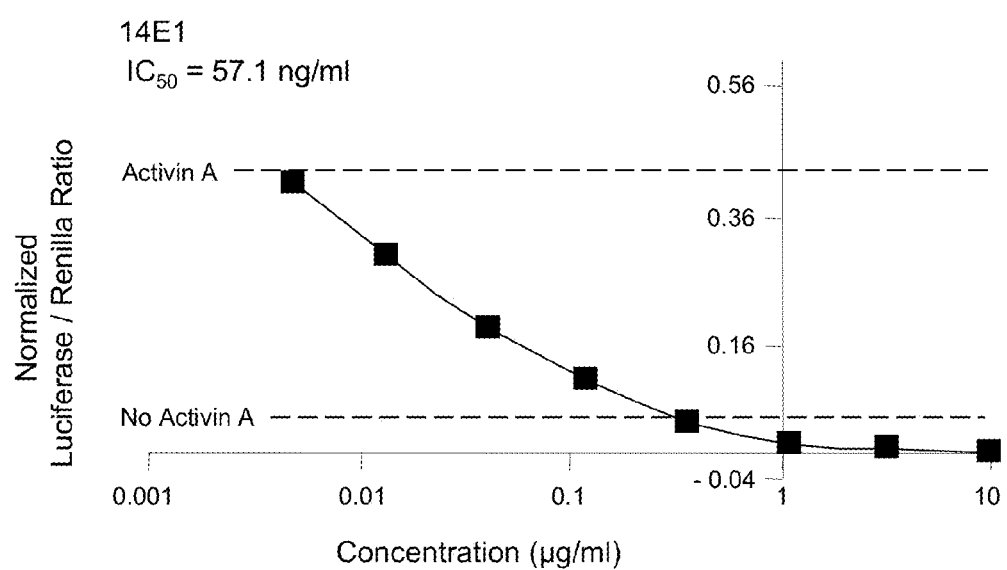

FIG. 13 depicts the ability of Ab-14E1 to neutralize activin A-mediated signaling in a cell-based assay. In A204 cells, where effects of activin A on reporter gene expression are mediated mainly by ActRIIA, Ab-14E1 inhibited activin A-stimulated gene expression in a concentration-dependent manner with an $IC_{50}$ of 57.1 ng/ml.

Figure 14:
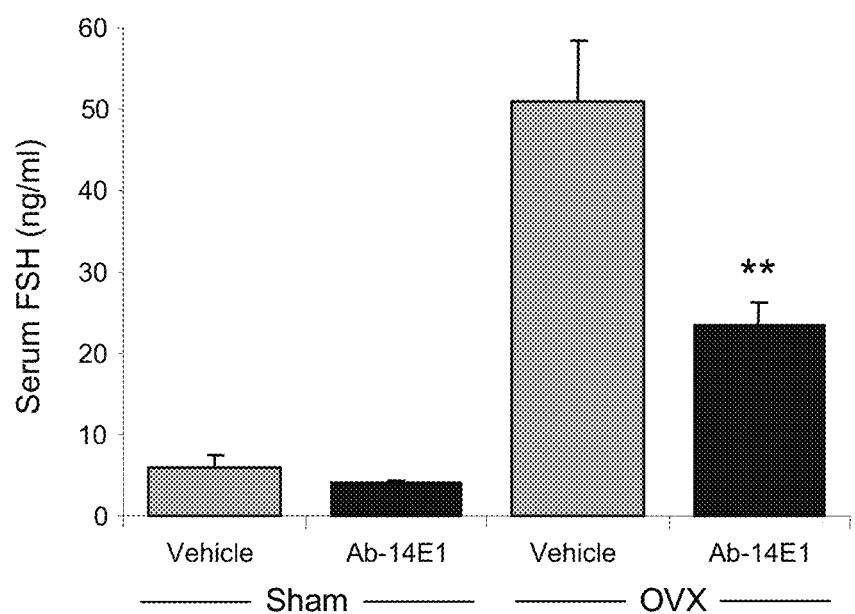

FIG. 14 depicts the effect of Ab-14E1 on serum levels of follicle-stimulating hormone (FSH) in ovariectomized (OVX) or sham-operated mice. Means±SEM; **, $p<0.01$ vs. OVX+vehicle. Treatment with Ab-14E1 reduced FSH levels in OVX mice by more than 50%.

Figure 15:
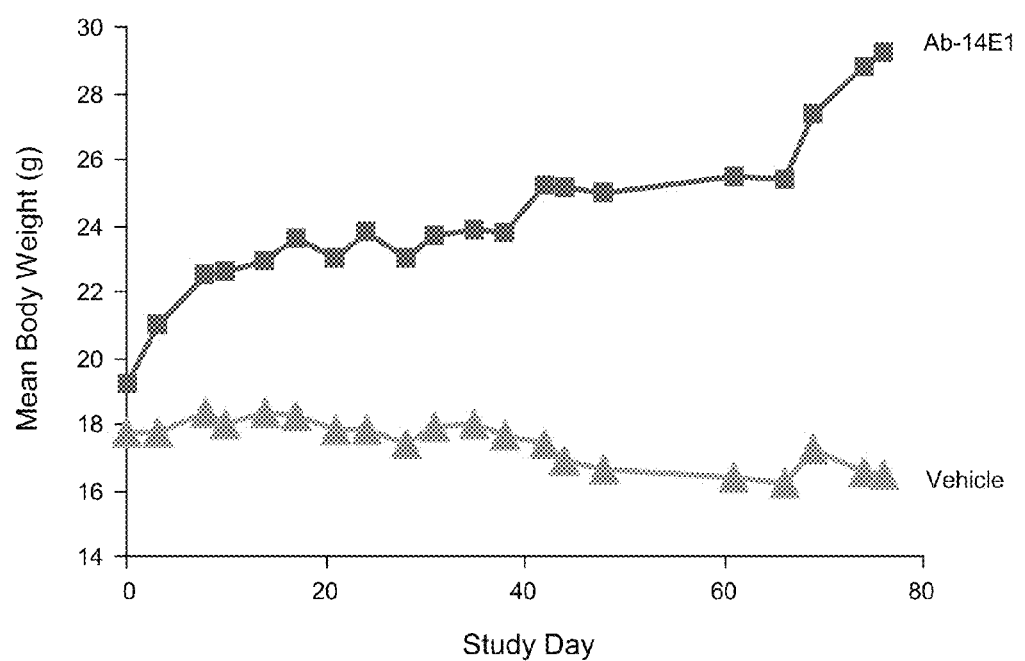

FIG. 15 depicts the effect of Ab-14E1 on body weight in inhibin-deficient male mice which succumb to a cancer cachexia-like syndrome. Concurrent dosing and weight measurement began on day 0 and continued until death of the animal; results through day 80 are shown. Treatment with Ab-14E1 alleviated tumor-dependent cachexia as evidenced by improved weight profiles compared to vehicle.

Figure 16:
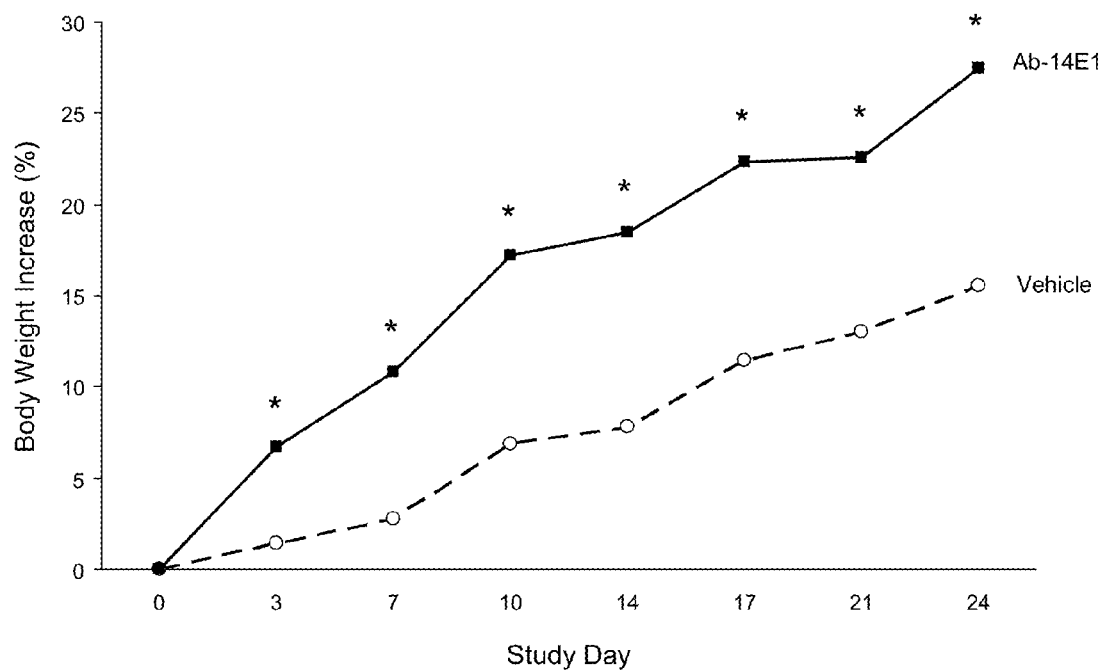

FIG. 16 depicts the effect of Ab-14E1 on body weight increase in normal mice. *, $p<0.05$ vs. vehicle on corresponding study days. Compared with controls, mice treated with Ab-14E1 showed significantly greater weight gain throughout the course of the study.

Figure 17:
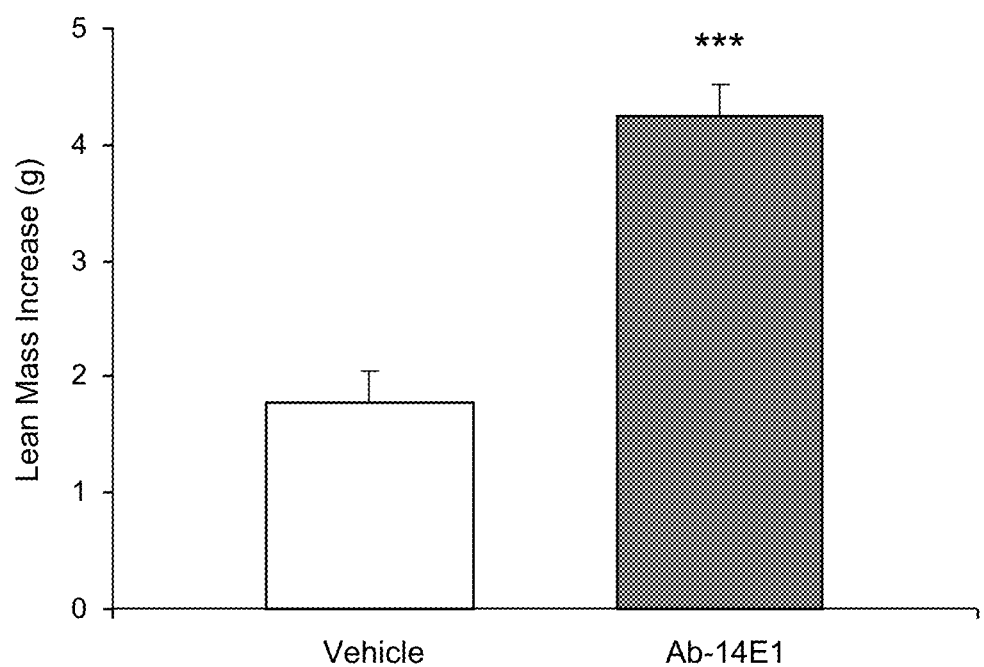

FIG. 17 depicts the effect of Ab-14E1 on lean mass increase in normal mice at study end as determined by whole-body NMR. ***, $p<0.001$ vs. vehicle. After 4 weeks of treatment, mice treated with Ab-14E1 gained more than twice as much lean mass as controls.

DETAILED DESCRIPTION OF THE INVENTION

1. Overview

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Activins are dimeric polypeptide growth factors that belong to the TGF-beta superfamily. There are three principal activin forms (A, B, and AB) that are homo/heterodimers of two closely related β subunits ($\beta_A\beta_A$, $\beta_B\beta_B$, and $\beta_A\beta_B$). The human genome also encodes an activin C and an activin E, which are primarily expressed in the liver. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from stimulated human monocytic leukemic cells was found to be identical to activin A (Murata et al., 1988, PNAS, 85:2434). It has been suggested that activin A acts as a natural, positive regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin.

Activin signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIA and ActRIIB, have been identified as the type II receptors for activins A, B, AB, C and E (Mathews and Vale, 1991, Cell 65:973-982; Attisano et al., 1992, Cell 68: 97-108). Besides activins, ActRIIA and ActRIIB can interact biochemically with several other TGF-β family proteins, including BMP7, Nodal, BMP9, BMP10, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

Inhibitors of the activin signaling pathway have been proposed for treatment of a variety of disorders, including muscle loss, excessive FSH, obesity, bone loss, various tumors including multiple myeloma and breast cancer, and anemia. To our knowledge, no antibody has been generated that binds to ActRIIA and inhibits signaling by members of the TGF-beta superfamily. While ActRIIA has been known for almost twenty years, it is possible that the high conservation between human, murine and other vertebrate ActRIIA sequences, coupled with the reported lethality of ActRIIA knockout animals has prevented the production of neutralizing anti-ActRIIA antibodies. As demonstrated herein, anti-ActRIIA antibodies that neutralize ActRIIA signaling can be produced, and this disclosure provides extensive structural and functional characterization to make a broad array of neutralizing anti-ActRIIA antibodies and fragments thereof accessible.

As shown herein, neutralizing anti-ActRIIA antibodies may be used in a variety of indications, including the treatment of cancer and cachexia as well as to reduce FSH levels in patients in need thereof.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue. Unless indicated otherwise, BLAST shall be the default algorithm for comparisons.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

As used herein, the term "ActRIIA" refers to a family of activin receptor type IIA (ActRIIA) proteins from any species and variants derived from such ActRIIA proteins. Reference to ActRIIA herein is understood to be a reference to any one of the currently identified forms. Members of the ActRIIA family are generally transmembrane proteins, composed of a ligand-binding extracellular domain with a cysteine-rich region, a transmembrane domain, and a cytoplasmic domain with predicted serine/threonine kinase activity.

The human ActRIIA precursor protein sequence is as follows, with the underlined sequence corresponding to the literature-reported mature extracellular domain, within which are epitopes targeted by neutralizing anti-ActRIIA antibodies and other ActRIIA binding agents.

(SEQ ID NO: 1)
MGAAAKLAFAVFLISCSSGAILGRSETQECLFFNANWEKDRTNQTGVEP

CYGDKDKRRHCFATWKNISGSIEIVKQGCWLDDINCYDRTDCVEKKDSP

EVYFCCCEGNMCNEKFSYFPEMEVTQPTSNPVTPKPPYYNILLYSLVPL

MLIAGIVICAFWVYRHHKMAYPPVLVPTQDPGPPPPSPLLGLKPLQLLE

VKARGRFGCVWKAQLLNEYVAVKIFPIQDKQSWQNEYEVYSLPGMKHEN

ILQFIGAEKRGTSVDVDLWLITAFHEKGSLSDFLKANVVSWNELCHIAE

TMARGLAYLHEDIPGLKDGHKPAISHRDIKSKNVLLKNNLTACIADFGL

ALKFEAGKSAGDTHGQVGTRRYMAPEVLEGAINFQRDAFLRIDMYAMGL

VLWELASRCTAADGPVDEYMLPFEEEIGQHPSLEDMQEVVVHKKKRPVL

RDYWQKHAGMAMLCETIEECWDHDAEARLSAGCVGERITQMQRLTNIIT

TEDIVTVVTMVTNVDFPPKESSL

The nucleic acid sequence encoding human ActRIIA precursor protein is as follows (nucleotides 164-1705 of Genbank entry NM 001616):

(SEQ ID NO: 2)
ATGGGAGCTGCTGCAAAGTTGGCGTTTGCCGTCTTTCTTATCTCCTGTT

CTTCAGGTGCTATACTTGGTAGATCAGAAACTCAGGAGTGTCTTTTCTT

TAATGCTAATTGGGAAAAAGACAGAACCAATCAAACTGGTGTTGAACCG

TGTTATGGTGACAAAGATAAACGGCGGCATTGTTTTGCTACCTGGAAGA

ATATTTCTGGTTCCATTGAAATAGTGAAACAAGGTTGTTGGCTGGATGA

TATCAACTGCTATGACAGGACTGATTGTGTAGAAAAAAAAGACAGCCCT

GAAGTATATTTTTGTTGCTGTGAGGGCAATATGTGTAATGAAAAGTTTT

CTTATTTTCCAGAGATGGAAGTCACACAGCCCACTTCAAATCCAGTTAC

ACCTAAGCCACCCTATTACAACATCCTGCTCTATTCCTTGGTGCCACTT

ATGTTAATTGCGGGGATTGTCATTTGTGCATTTTGGGTGTACAGGCATC

ACAAGATGGCCTACCCTCCTGTACTTGTTCCAACTCAAGACCCAGGACC

ACCCCCACCTTCTCCATTACTAGGGTTGAAACCACTGCAGTTATTAGAA

GTGAAAGCAAGGGGAAGATTTGGTTGTGTCTGGAAAGCCCAGTTGCTTA

ACGAATATGTGGCTGTCAAAATATTTCCAATACAGGACAAACAGTCATG

GCAAAATGAATACGAAGTCTACAGTTTGCCTGGAATGAAGCATGAGAAC

ATATTACAGTTCATTGGTGCAGAAAAACGAGGCACCAGTGTTGATGTGG

ATCTTTGGCTGATCACAGCATTTCATGAAAAGGGTTCACTATCAGACTT

TCTTAAGGCTAATGTGGTCTCTTGGAATGAACTGTGTCATATTGCAGAA

ACCATGGCTAGAGGATTGGCATATTTACATGAGGATATACCTGGCCTAA

AAGATGGCCACAAACCTGCCATATCTCACAGGGACATCAAAAGTAAAAA

TGTGCTGTTGAAAAACAACCTGACAGCTTGCATTGCTGACTTTGGGTTG

GCCTTAAAATTTGAGGCTGGCAAGTCTGCAGGCGATACCCATGGACAGG

TTGGTACCCGGAGGTACATGGCTCCAGAGGTATTAGAGGGTGCTATAAA

-continued

```
CTTCCAAAGGGATGCATTTTTGAGGATAGATATGTATGCCATGGATTA

GTCCTATGGGAACTGGCTTCTCGCTGTACTGCTGCAGATGGACCTGTAG

ATGAATACATGTTGCCATTTGAGGAGGAAATTGGCCAGCATCCATCTCT

TGAAGACATGCAGGAAGTTGTTGTGCATAAAAAAAAGAGGCCTGTTTTA

AGAGATTATTGGCAGAAACATGCTGGAATGGCAATGCTCTGTGAAACCA

TTGAAGAATGTTGGGATCACGACGCAGAAGCCAGGTTATCAGCTGGATG

TGTAGGTGAAAGAATTACCCAGATGCAGAGACTAACAAATATTATTACC

ACAGAGGACATTGTAACAGTGGTCACAATGGTGACAAATGTTGACTTTC

CTCCCAAAGAATCTAGTCTATGA
```

2. ActRIIA Binding Agents

The present invention relates in part to regions of the ActRIIA protein that contain epitopes recognized by antibodies that also bind to full-length ActRIIA, and methods of making and using these epitopes. The invention also provides binding agents (such as antibodies) that specifically bind to ActRIIA or portions of ActRIIA, and methods for using such binding agents. The binding agents are useful to block or impair the binding of human ActRIIA to one or more ligand(s) and to interfere with its biological activity.

It will be understood by one of skill in the art that there is a high degree of sequence identity between the orthologs of ActRIIA. A murine ortholog of human ActRIIA has been described (NCBI Ref. Seq.: NP_031422) that differs by only two substitutions in the mature 494-amino-acid protein, while a rat ortholog has been described (NCBI Ref. Seq.: NP_113759) that differs by only three substitutions. Accordingly, agents binding to human ActRIIA will be expected to bind to murine ActRIIA or rat ActRIIA in cases where the recognition site of the binding agent, e.g., an antibody binding site such as an epitope, is highly conserved and in particular nearly or completely identical to the human sequence. Thus, when the term "specific binding to ActRIIA" is used, it is understood to include binding to multiple species of ActRIIA where the sequences between species are conserved.

Examples of binding agents according to the invention include the antibody 14E1 (Ab-14E1). As used herein, Ab-14E1 comprises the polypeptides expressed by the nucleotides shown in SEQ ID NOs: 14 and 15.

Binding agents of the invention are typically antibodies or fragments thereof, as defined herein. The term "antibody" refers to an intact antibody, or a binding fragment thereof. An antibody may comprise a complete antibody molecule (including polyclonal, monoclonal, chimeric, humanized, or human versions having full-length heavy and/or light chains), or comprise an antigen-binding fragment thereof. Antibody fragments include F(ab')$_2$, Fab, Fab', Fv, Fc, and Fd fragments, and can be incorporated into single-domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1 126-1136). Antibody-like polypeptides are also disclosed in U.S. Pat. No. 6,703,199 ["Artificial Antibody Polypeptides", assigned to Research Corp Technologies], including fibronectin polypeptide monobodies. Other antibody-like polypeptides are disclosed in U.S. patent publication 2005/0238646, which are single-chain polypeptides. As used herein, the isolated antibody or an antigen-binding fragment thereof may be a polyclonal antibody, a monoclonal antibody, a humanized antibody, a human antibody, a chimeric antibody, or the like. In each of these types of binding agents, it is generally expected that one would insert one or more CDRs from the antibodies disclosed herein to produce an alternative ActRIIA binding agent.

An antibody according to the present invention may belong to any immunoglobin class, for example IgG (including IgG1, IgG2, IgG3, IgG4 and IgG2/4 hybrids), IgE, IgM, IgD, or IgA. It may be obtained from or derived from an animal, for example, birds (e.g., chicken) and mammals, which include but are not limited to a mouse, rat, hamster, rabbit, cow, horse, sheep, goat, camel, human, or other primate. The antibody may be an internalizing antibody.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 55 fragment termed F(ab')$_2$. This fragment can be further cleaved using a thiol reducing agent to produce 3.5S Fab monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single-chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable regions") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies. Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)).

Thus, in one embodiment, the binding agent comprises at least one CDR as described herein. The binding agent may comprise at least two, three, four, five or six CDRs, as described herein. The binding agent further may comprise at least one variable region domain of an antibody described herein. The variable region domain may be of any size or amino acid composition and will generally comprise at least one CDR sequence responsible for binding to human ActRIIA, for example CDR-H1, CDR-H2, CDR-H3, and/or the light chain CDRs specifically described herein and which are adjacent to or in frame with one or more framework sequences. In general terms, the variable (V) region domain may be any suitable arrangement of immunoglobulin heavy (VH) and/or light (VL) chain variable domains. Thus, for example, the V region domain may be monomeric and be a VH or VL domain, which is capable of independently binding human ActRIIA with an affinity at least equal to $1\times10^{-7}$M or less as described below. Alternatively, the V region domain may be dimeric and contain VH-VH, VH-VL, or VL-VL dimers. The V region dimer comprises at least one VH and at least one VL chain that may be non-covalently associated (hereinafter referred to as FV). If desired, the chains may be covalently coupled either directly, for example via a disulfide bond between the two variable domains, or through a linker, for example a peptide linker, to form a single chain Fv (scFV).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab fragment, or to provide further domains, such as antibody CH2 and CH3 domains.

As described herein, binding agents may comprise at least one of these CDRs. For example, one or more CDRs may be incorporated into known antibody framework regions (IgG1, IgG2, etc.), or conjugated to a suitable vehicle to enhance the half-life thereof. Suitable vehicles include, but are not limited to, Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337.

In certain embodiments, a derivative binding agent comprises one or more of monomethoxy-polyethylene glycol, dextran, cellulose, or other carbohydrate-based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymers is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

Antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., Nature 256:495, 1975; Coligan et al. (eds.), Current Protocols in Immunology, 1:2.5.12.6.7 (John Wiley & Sons 1991); U.S. Pat. Nos. RE 32,011, 4,902,614, 4,543,439, and 4,411,993; Monoclonal Antibodies, Hybridomas: A New Dimension in Biological Analyses, Plenum Press, Kennett, McKearn, and Bechtol (eds.) (1980); and Antibodies: A Laboratory Manual, Harlow and Lane (eds.), Cold Spring Harbor Laboratory Press (1988); Picksley et al., "Production of monoclonal antibodies against proteins expressed in *E. coli*," in DNA Cloning 2: Expression Systems, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, rabbit, or preferably a mouse, preferably an ActRIIA-deficient mouse, with an immunogen comprising human ActRIIA of SEQ ID NO: 1, or a fragment thereof, according to methods known in the art and described herein. As ActRIIA-deficient mice (i.e. Acvr2$^{-/-}$ knockout mice) have substantially decreased viability and other defects, care will be needed to obtain sufficiently healthy and properly bred mice. The presence of specific antibody production may be monitored after the initial injection and/or after a booster injection by obtaining a serum sample and detecting the presence of an antibody that binds to human ActRIIA or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human ActRIIA, using any one of a variety of immunoassays known in the art and described herein. The hybridomas are cloned (e.g., by limited dilution cloning or by soft agar plaque isolation) and positive clones that produce an antibody specific to ActRIIA are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand whose selection is based on particular properties of the antibody (e.g., heavy- or light-chain isotype, binding specificity, etc.). Examples of a suitable ligand, immobilized on a solid support, include Protein A, Protein G, an anti-constant region (light chain or heavy chain) antibody, an anti-idiotype antibody, and an ActRIIa protein, or fragment or variant thereof.

It will be appreciated by one of skill in the art that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative and that do not destroy the ActRIIA binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Conservative Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |

TABLE 1-continued

Conservative Substitutions

| Original Residue | Exemplary Substitutions | Preferred Substitutions |
|---|---|---|
| Glu (E) | Asp; Gln | Asp |
| Gly (G) | Ala | Ala |
| His (H) | Arg; Asn; Gln; Lys | Arg |
| Ile (I) | Leu; Val; Met; Ala; Phe; Norleucine | Leu |
| Leu (L) | Ile; Norleucine; Val; Met; Ala; Phe | Ile |
| Lys (K) | Arg; Gln; Asn | Arg |
| Met (M) | Leu; Phe; Ile | Leu |
| Phe (F) | Tyr; Trp; Leu; Val; Ile; Ala | Tyr |
| Pro (P) | Ala | Ala |
| Ser (S) | Thr | Thr |
| Thr (T) | Ser; Val | Ser |
| Trp (W) | Tyr; Phe | Tyr |
| Tyr (Y) | Phe; Trp; Thr; Ser | Phe |
| Val (V) | Leu; Ile; Norleucine; Met; Phe; Ala | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) hydrophobic: Met, Ala, Val, Leu, Ile, Norleucine;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro; and
  (6) aromatic: Trp, Tyr, Phe.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the nonhomologous regions of the molecule.

Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

The disclosure includes results of x-ray crystallographic analysis of monoclonal Ab-14E1 Fab fragment complexed with the extracellular domain (ECD) of human ActRIIA. As detailed in the Examples, analyses have identified 17 amino acid residues in Ab-14E1 VH (SEQ ID NO: 12) and 16 residues in Ab-14E1 VL (SEQ ID NO: 13) that make contact with amino acids in human ActRIIA ECD and can therefore be considered specificity-determining residues (SDRs) (Padlan et al., FASEB J 9:133-139 (1995)). The vast majority of these SDRs are clustered within the CDRs. Two more SDRs are located immediately adjacent to CDRs, the first a glycine preferentially located next to CDR-H1 and +4 residues from the first conserved cysteine ($C_1$). Variants are contemplated comprising a glycine located +3 or +5 residues from $C_1$ in SEQ ID NO: 12. The second such SDR is a tyrosine preferentially located next to CDR-L2 and +26 residues from $C_1$, and variants are contemplated with a tyrosine located +24, +25, +27, or +28 residues from $C_1$ in SEQ ID NO: 13. Finally, two additional ("satellite") SDRs are located well outside CDRs, the first a valine preferentially located −20 residues from $C_1$ in SEQ ID NO: 12, and the second a serine preferentially located −21 residues from the second conserved cysteine ($C_2$) in SEQ ID NO: 13. Variants are envisioned comprising a valine located −18, −19, −21, or −22 residues from $C_1$ in SEQ ID NO: 12 or comprising a serine located −19, −20, −22, or −23 residues from $C_2$ in SEQ ID NO: 13. It is expected that only conservative mutations will be tolerated, if at all, at the 33 SDR positions and at non-SDR positions within the CDRs. Variants are contemplated, particularly those having at least 80%, 85%, 90%, 95%, or 99% identity to the corresponding portions of SEQ ID NOs: 4, 5, 6, 7, 8, and 9. In framework regions outside the SDRs and CDRs, it is expected that non-conservative mutations will be tolerated, and variants are contemplated having at least 75%, 80%, 85%, 90%, 95%, or 99% identity to the corresponding portions of SEQ ID NOs: 12 and 13.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or sequence similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(0:244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

It will be understood by one skilled in the art that some proteins, such as antibodies, may undergo a variety of posttranslational modifications during expression and secretion from host cells. The type and extent of these modifications often depends on the host cell line used to express the protein as well as the culture conditions. Such modifications may include variations in glycosylation, methionine or tryptophan oxidation, diketopiperizine formation, aspartate isomerization and asparagine deamidation. A frequent modification is the loss of a carboxy-terminal basic residue (such as lysine or arginine) due to the action of carboxy-peptidases (as described in Harris, R J. Journal of Chromatography 705:129-134, 1995). Once the proteins have been expressed and processed they are in a 'mature' form. Thus it is understood that the invention includes mature antibodies that result from expression of the DNAs of the invention.

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Amino acid substitutions (whether conservative or non-conservative) can be determined by those skilled in the art at the time such substitutions are desired. In certain embodiments, amino acid substitutions can be used to identify important residues of antibodies to ActRIIA, or to increase or decrease the affinity of the antibodies to ActRIIA described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides.

According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids (e.g., CDRs, a variable region, etc.) that bind to an antigen in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria, or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LAC1-D1, Z domain and tendramisat domains may be used (See e.g., Nygren and Uhlen, 1997, Current Opinion in Structural Biology, 7, 463-469).

In preferred embodiments, it will be appreciated that the binding agents of the invention include humanized antibodies, which can be produced using techniques known to those skilled in the art (Zhang, W., et al., Molecular Immunology. 42(12): 1445-1451, 2005; Hwang W. et al., Methods. 36(1): 35-42, 2005; Dall'Acqua W F, et al., Methods 36(1):43-60, 2005; and Clark, M., Immunology Today. 21(8):397-402, 2000).

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., Nature Genet. 7:13, 1994; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N. Y Acad. Sci. 764:525-35. In this technique, elements of the human heavy- and light-chain locus are introduced into strains of mice derived from embryonic stem cell lines that contain targeted disruptions of the endogenous heavy-chain and light-chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for ActRIIA. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to ActRIIA can be identified by immunodetection methods as provided herein, for example, an ELISA, and then isolated by standard cloning techniques. The stability of the lymphoblastoid cell line producing an anti-ActRIIA antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B cells with human ActRIIA, followed by fusion of primed B cells with a heterohybrid fusion partner. See, e.g., Boerner et al., 1991, J. Immunol. 147:86-95.

In certain embodiments, a B cell that is producing an anti-human ActRIIA antibody is selected and the light chain and heavy chain variable regions are cloned from the B cell according to molecular biology techniques known in the art (WO 92/02551; U.S. Pat. No. 5,627,052; Babcook et al., Proc. Natl. Acad. Sci. USA 93:7843-48 (1996)) and described herein. B cells from an immunized animal may be isolated from the spleen, lymph node, or peripheral blood sample by selecting a cell that is producing an antibody that specifically binds to ActRIIA. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human ActRIIA. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

Additionally, one skilled in the art will recognize that suitable binding agents include portions of these antibodies, such as one or more of CDR-H1, CDR-H2, CDR-H3, CDR-L1, CDR-L2 and CDR-L3, as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. CDRs may be altered to increase or decrease length as well, and thus changes that are characterized as substitutions, insertions and deletions are all contemplated. The non-CDR portion of the binding agent may be a non-protein molecule, wherein the binding agent cross-blocks the binding of an antibody disclosed herein to ActRIIA and/or neutralizes ActRIIA. The non-CDR portion of the binding agent may be composed of amino acids, wherein the binding agent is a recombinant binding protein or a synthetic peptide, and the recombinant binding protein cross-blocks the binding of an antibody disclosed herein to ActRIIA and/or neutralizes ActRIIA. The non-CDR portion of the binding agent may be composed of amino acids, wherein the binding agent is a recombinant binding protein, and the recombinant binding protein exhibits a similar binding pattern to human ActRIIA peptides in the human ActRIIA peptide epitope competition binding assay (described hereinbelow) as that exhibited by antibody Ab-14E1, and/or neutralizes ActRIIA.

In one embodiment, it is contemplated that one can use the antibody heavy chain as 'bait' in a library screen where the library is composed of human antibody light chains, to identify complementing human light chains where the reconstituted antibody binds to ActRIIA. In this embodiment, the heavy chain is from an antibody specific to ActRIIA and is mouse, chimeric, or humanized.

Where an antibody comprises one or more of CDR-H1, CDR-H2, CDR-H3, CDR-L1, CDR-L2, and CDR-L3, as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 Methods Enzymol. 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. To obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (Molecular Cloning, A Laboratory Manual, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International pic sequencing handbook, and site directed mutagenesis can be carried out according to methods known in the art (Kramer et al., Nucleic Acids Res. 12:9441, (1984); Kunkel Proc. Natl. Acad. Sci. USA 82:488-92 (1985); Kunkel et al., Methods in Enzymol. 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in Biotechnology and Genetic Engineering Reviews (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs, improved antibodies can be obtained by a number of affinity maturation protocols including maintaining the CDRs (Yang et al., J. MoI. Biol., 254, 392-403, 1995), chain shuffling (Marks et al., Bio/Technology, 10, 779-783, 1992), use of mutation strains of *E. coli.* (Low et al., J. MoI. Biol., 250, 350-368, 1996), DNA shuffling (Patten et al., Curr. Opin. Biotechnol., 8, 724-733, 1997), phage display (Thompson et al., J. MoI. Biol., 256, 7-88, 1996) and sexual PCR (Crameri, et al., Nature, 391, 288-291, 1998). All of these methods of affinity maturation are discussed by Vaughan et al. (Nature Biotechnology, 16, 535-539, 1998).

An additional method for obtaining antibodies of the invention is by phage display. See, e.g., Winter et al., 1994 Annu Rev. Immunol. 12:433-55; Burton et al., 1994 Adv. Immunol. 57:191-280. Combinatorial libraries of human or murine immunoglobulin variable-region genes may be created in phage vectors that can be screened to select Ig fragments (Fab, Fv, sFv, or multimers thereof) that bind specifically to ActRIIA or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M 13 or a variant thereof, in frame with the sequence encoding a phage coat protein. A fusion protein may be a fusion of the coat protein with the light chain variable-region domain and/or with the heavy chain variable-region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using lambda ImmunoZap™ (H) and lambda ImmunoZap™ (L) vectors (Stratagene, La Jolla, Calif.). Briefly, mRNA is isolated from a B cell population, and used to create heavy and light chain immunoglobulin cDNA expression libraries in the lambda ImmunoZap(H) and lambda ImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from E. coli.

In one embodiment in a hybridoma, the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for VHa, VHb, VHc, VHd, CHl, VL and CL regions.) These primers may be used to amplify heavy or light chain variable regions, which may then be inserted into vectors such as ImmunoZAP™ H or ImmunoZAP™ (Stratagene), respectively. These vectors may then be introduced into E. coli, yeast, or mammalian-based systems for expression. Large amounts of a single-chain protein containing a fusion of the VH and VL domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents bind specifically to ActRIIA. As with all binding agents and binding assays, one of skill in this art recognizes that the various moieties which a binding agent should not detectably bind in order to be therapeutically effective and suitable would be exhaustive and impractical to list. Therefore, for a binding agent disclosed herein, the term "specifically binds" refers to the ability of a binding agent to bind to ActRIIA, preferably human ActRIIA, with greater affinity than it binds to an unrelated control protein. Preferably the control protein is hen egg white lysozyme. Preferably the binding agents bind to ActRIIA with an affinity that is at least, 50, 100, 250, 500, 1000, or 10,000 times greater than the affinity for a control protein. A binding agent may have a binding affinity for human ActRIIA of less than or equal to $1\times10^{-7}$M, less than or equal to $1\times10^{-8}$M, less than or equal to $1\times10^{-9}$M, less than or equal to $1\times10^{-10}$ M, less than or equal to $1\times10^{-11}$ M, or less than or equal to $1\times10^{-12}$ M.

Affinity may be determined by an affinity ELISA assay. In certain embodiments, affinity may be determined by a BIACORE™ assay. In certain embodiments, affinity may be determined by a kinetic method. In certain embodiments, affinity may be determined by an equilibrium/solution method. Such methods are described in further detail herein or known in the art.

The affinity of a binding agent such as an antibody or binding partner, as well as the extent to which a binding agent (such as an antibody) inhibits binding, can be determined by one of ordinary skill in the art using conventional techniques, for example by surface plasmon resonance (SPR; BIACORE™, Biosensor, Piscataway, N.J.) or according to methods described by Scatchard et al. (Ann. N.Y. Acad. Sci. 51:660-672 (1949)). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-65 (1993)).

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to at least one of the CDRs depicted in the Examples (SEQ ID NOs: 4, 5, 6, 7, 8, and 9); and/or to a CDR of an ActRIIA binding agent that cross-blocks the binding of Ab-14E1 to ActRIIA, and/or is cross-blocked from binding to ActRIIA by Ab-14E1; and/or to a CDR of an ActRIIA binding agent wherein the binding agent can block the effect of ActRIIA in a cell-based assay (i.e. an ActRIIA neutralizing binding agent).

Examples of ActRIIA binding agent polypeptides and antibodies that are within the scope of the invention are those that have amino acid sequences that are at least 85%, 86%, 87%, 88%, 89%, 90%, 91%, 92%, 93%, 94%, 95%, 96%, 97%, 98% or 99% identical to a variable region of Ab-14E1 (SEQ ID NOs: 12 and 13), and cross-block the binding of Ab-14E1 to ActRIIA, and/or are cross-blocked from binding to ActRIIA by Ab-14E1; and/or can block the inhibitory effect of ActRIIA in a cell-based assay (i.e. an ActRIIA neutralizing binding agent); and/or bind to one or more of the contact residues described in the Examples, below.

Examples of polynucleotides encoding ActRIIA binding agents that are within the scope of the invention are those that have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of Ab-14E1 (SEQ ID NOs: 15 and 16), and wherein the encoded ActRIIA binding agents cross-block the binding of Ab-14E1 to ActRIIA, and/or are cross-blocked from binding to ActRIIA by Ab-14E1; and/or can block the inhibitory effect of ActRIIA in a cell-based assay (i.e. an ActRIIA neutralizing binding agent); or bind to one or more of the contact residues described in the Examples, below.

ActRIIA binding agents of the present invention preferably modulate ActRIIA function in the cell-based assay described herein and/or the in vivo assay described herein and/or bind to one or more of the contact residues of ActRIIA described in the Examples below and/or cross-block the binding of antibody Ab-14E1 described in this application and/or are cross-blocked from binding ActRIIA by the antibody Ab-14E1 described in this application. Accordingly, such binding agents can be identified using the assays described herein.

In certain embodiments, binding agents are generated by first identifying antibodies that bind to one or more of the contact residues of ActRIIA described in the Examples and/or neutralize in the cell-based and/or in vivo assays described herein and/or cross-block the antibody Ab-14E1 described in this application and/or are cross-blocked from binding ActRIIA by antibody Ab-14E1 described in this application. The CDR regions from these antibodies are then used to insert into appropriate biocompatible frameworks to generate ActRIIA binding agents. The non-CDR portion of the binding agent may be composed of amino acids, or may be a nonprotein molecule. The assays described herein allow the characterization of binding agents. Preferably the binding agents of the present invention are antibodies as defined herein.

In the methods described herein to generate antibodies according to the invention, including the manipulation of the specific Ab-14E1 CDRs into new frameworks and/or constant regions, appropriate assays are available to select the desired antibodies or binding agents (i.e. assays for determining binding affinity to ActRIIA; cross-blocking assays such as the BIACORE™-based human ActRIIA peptide epitope competition binding assay described in Example 4 below; A204 cell-based assay; in vivo assays).

The terms "cross-block", "cross-blocked" and "cross-blocking" are used interchangeably herein to mean the ability of an antibody or other binding agent to interfere with the binding of other antibodies or binding agents to ActRIIA.

The extent to which an antibody or other binding agent is able to interfere with the binding of another to ActRIIA, and therefore whether it can be said to cross-block according to the invention, can be determined using competition binding assays. One particularly suitable quantitative assay uses a BIACORE™ instrument which can measure the extent of interactions using surface plasmon resonance technology. Example 4 provides methods for conducting a BIACORE™ based cross-blocking assay. Another suitable quantitative cross-blocking assay uses an ELISA-based approach to measure competition between antibodies or other binding agents in terms of their binding to ActRIIA.

The following generally describes a suitable BIACORE™ assay for determining whether an antibody or other binding agent cross-blocks or is capable of cross-blocking according to the invention. For convenience, reference is made to two antibodies, but it will be appreciated that the assay can be used with any of the ActRIIA binding agents described herein. The BIACORE™ instrument (for example the BIACORE™ 3000) is operated according to the manufacturer's recommendations.

Thus in one cross-blocking assay, ActRIIA-mFc fusion protein is captured on a CM5 BIACORE™ chip by previously attached anti-mFc IgG to generate an ActRIIA-coated surface. Typically 200-800 resonance units of ActRIIA-mFc (dimeric) would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of ActRIIA binding sites on that antibody.

The concentration of each antibody in the test mix should be high enough to readily saturate the binding sites for that antibody on the ActRIIA-mFc molecules captured on the BIACORE™ chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the ActRIIA-mFc-coated BIACORE™ chip and the total amount of binding recorded. The chip is then treated in such a way as to remove the bound antibodies without damaging the chip-bound ActRIIA-mFc. Typically, this is done by treating the chip with 30 mM HCl for 60 seconds.

The solution of antibody A* alone is then passed over the ActRIIA-mFc-coated surface and the amount of binding recorded. The chip is again treated to remove all of the bound antibody without damaging the chip-bound ActRIIA-mFc.

The solution of antibody B* alone is then passed over the ActRIIA-mFc-coated surface and the amount of binding recorded.

The maximum theoretical binding of the mixture of antibody A* and antibody B* is next calculated, and is the sum of the binding of each antibody when passed over the ActRIIA surface alone. If the actual recorded binding of the mixture is less than this theoretical maximum then the two antibodies are cross-blocking each other.

Thus, in general, a cross-blocking antibody or other binding agent according to the invention is one which will bind to ActRIIA in the above BIACORE™ cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The BIACORE™ assay described above is an assay used to determine if antibodies or other binding agents cross-block each other according to the invention. On rare occasions, particular antibodies or other binding agents may not bind to ActRIIA-mFc coupled via anti-mFc IgG to a CM5 BIACORE™ chip (this might occur when the relevant binding site on ActRIIA is masked or destroyed by ActRIIA linkage to mFc). In such cases, cross-blocking can be determined using a tagged version of ActRIIA, for example C-terminal His-tagged ActRIIA. In this particular format, an anti-His antibody would be coupled to the BIACORE™ chip and then the His-tagged ActRIIA would be passed over the surface of the chip and captured by the anti-His antibody. The cross-blocking analysis would be carried out essentially as described above, except that after each chip regeneration cycle, new His-tagged ActRIIA would be loaded back onto the surface coated with anti-His antibody. Moreover, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an anti-ActRIIA antibody or other ActRIIA binding agent cross-blocks or is capable of cross-blocking according to the invention. For convenience, reference is made to two antibodies, but it will be appreciated that the assay can be used with any of the ActRIIA binding agents described herein.

The general principle of the assay is to have an anti-ActRIIA antibody coated onto the wells of an ELISA plate. An excess amount of a second, potentially cross-blocking, anti-ActRIIA antibody is added in solution (i.e. not bound to the ELISA plate). A limited amount of ActRIIA (or alternatively ActRIIA-mFc) is then added to the wells. The coated antibody and the antibody in solution compete for binding of the limited number of ActRIIA (or ActRIIA-mFc) molecules. The plate is washed to remove ActRIIA that has not been bound by the coated antibody and to also remove the second, solution-phase antibody as well as any complexes formed between the second, solution-phase antibody and ActRIIA. The amount of bound ActRIIA is then measured using an appropriate ActRIIA detection reagent. An antibody in solution that is able to cross-block the coated antibody will be able to cause a decrease in the number of ActRIIA molecules that the coated antibody can bind relative to the number of ActRIIA molecules that the coated antibody can bind in the absence of the second, solution-phase antibody.

This assay is described here in more detail for Ab-14E1 and a theoretical antibody Ab-XX. In the instance where Ab-14E1 is chosen to be the immobilized antibody, it is coated onto the wells of the ELISA plate, after which the plates are blocked with a suitable blocking solution to minimize non-specific binding of reagents that are subsequently added. An excess amount of Ab-XX is then added to the ELISA plate such that the moles of Ab-XX ActRIIA binding sites per well are at least 10-fold higher than the moles of Ab-14E1 ActRIIA binding sites that were used, per well, during the coating of the ELISA plate.

ActRIIA is then added such that the moles of ActRIIA added per well are at least 25-fold lower than the moles of Ab-14E1 ActRIIA binding sites that were used for coating each well. Following a suitable incubation period the ELISA plate is washed and an ActRIIA detection reagent is added to measure the amount of ActRIIA specifically bound by the coated anti-ActRIIA antibody (in this case Ab-14E1). The background signal for the assay is defined as the signal obtained in wells with the coated antibody (in this case Ab-14E1), solution-phase antibody (in this case Ab-XX), ActRIIA buffer only (i.e. no ActRIIA) and ActRIIA detection reagents. The positive control signal for the assay is defined as the signal obtained in wells with the coated antibody (in this case Ab-14E1), solution-phase antibody buffer only (i.e. no solution-phase antibody), ActRIIA and ActRIIA detection reagents. The ELISA assay needs to be run in such a manner so as to have the positive control signal at least 3 times the background signal.

As a control for methodologic artifacts, the cross-blocking assay may be run in the format just described and also reversed, with Ab-XX as the coated antibody and Ab-14E1 as the solution-phase antibody.

A reporter-gene assay with A204 rhabdomyosarcoma cells may be used to determine whether a given anti-ActRIIA antibody can neutralize activation of intrinsic ActRIIA by recombinant ActRIIA ligands such as activin A and activin B. In the absence of antibody, these ActRIIA ligands can dose-dependently stimulate ActRIIA signaling in A204 cells.

To begin the assay, A204 cells (ATCC HTB-82) are distributed in 48-well plates at $10^5$ cells per well. On the next day, cells are transfected with primary reporter plasmid, pGL3(CAGA)12 (Dennler et al, 1998, EMBO 17:3091-3100), and a Renilla reporter plasmid, pRLCMV, which is used to control for transfection efficiency. The CAGA12 motif is present in TGF-beta-responsive genes, so this vector is of general use for factors signaling through Smad2 and Smad3. A solution containing 10 μg pGL3(CAGA)12, 1 μg pRLCMV, 30 μl Fugene 6 (Roche Diagnostics), and 970 μl OptiMEM (Invitrogen) is preincubated for 30 min, then added to McCoy's growth medium, which is applied to the plated cells (500 μl/well) for incubation overnight at room temperature. On day 3, medium is removed and cells are incubated (250 μl/well) for 6 h at 37° C. with test substances diluted in phosphate-buffered saline containing 0.1% BSA. After rinsing, cells are lysed with passive lysis buffer (Promega E1941) and stored overnight at −70° C. On day 4, plates are warmed to room temperature with gentle shaking Cell lysates are transferred in duplicate to a chemoluminescence plate (96-well) and analyzed in a luminometer with reagents from a Dual-Luciferase Reporter Assay system (Promega E1980) to determine normalized luciferase activity.

Antibodies disclosed herein bind to regions of human ActRIIA which are important for the in vivo activity of the protein, thereby inhibiting the activity of ActRIIA. Binding of an antibody to ActRIIA can be correlated with changes in biomarkers associated with ActRIIA-mediated signaling, for example circulating FSH concentrations, body weight or markers of cachexia in animals with activin-dependent tumorigenesis.

Pharmacodynamic parameters dependent on ActRIIA signaling can be measured as endpoints for in vivo testing of ActRIIA binding agents in order to identify those binding agents that are able to neutralize ActRIIA and provide a therapeutic benefit. Such parameters include serum FSH concentrations in ovariectomized (OVX) females, lean body mass and fat content as shown in the Examples. An ActRIIA neutralizing binding agent is defined as one capable of causing a statistically significant change, as compared to vehicle-treated animals, in such a pharmacodynamic parameter. Such in vivo testing can be performed in any suitable mammal (e.g. mouse, rat, monkey).

3. Screening Assays and Other Biochemical Uses

In certain aspects, the present invention relates to the use of the subject ActRIIA binding agents to identify compounds (agents) which are agonist or antagonists of ActRIIA. Compounds identified through this screening can be tested to assess their ability to modulate ActRIIA-mediated signaling in vivo or in vitro. These compounds can be tested, for example, in animal models.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIA binding agent and an ActRIIA polypeptide.

Merely to illustrate, in an exemplary screening assay of the present invention, the compound of interest is contacted with an isolated and purified ActRIIA binding agent which is ordinarily capable of binding to an ActRIIA polypeptide, as appropriate for the intention of the assay. To the mixture of the compound and ActRIIA binding agent is then added a composition containing an ActRIIA polypeptide. Detection and quantification of complexes between ActRIIA polypeptide and ActRIIA binding agent provides a means for determining the compound's efficacy at inhibiting (or potentiating) complex formation between the ActRIIA polypeptide and ActRIIA binding agent. The efficacy of the compound can be assessed by generating dose response curves from data obtained using various concentrations of the test compound. Moreover, a control assay can also be performed to provide a baseline for comparison. For example, in a control assay, isolated and purified ActRIIA binding agent is added to a composition containing an ActRIIA polypeptide, and the formation of complexes between ActRIIA polypeptide and ActRIIA binding agent is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between ActRIIA polypeptide and ActRIIA binding agent may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIA polypeptide or ActRIIA binding agent, by immunoassay, or by chromatographic detection.

4. Formulation and Delivery of Therapeutics

Pharmaceutical compositions are provided, comprising one of the above-described binding agents such as antibody Ab-14E1 or a humanized version thereof, along with a pharmaceutically or physiologically acceptable carrier, excipient, or diluent.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. Prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, Remington's Pharmaceutical Sciences, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologies standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol. 16(7):307-21, 1998; Takakura, Nippon Rinsho 56(3):691-95, 1998; Chandran et al., Indian J. Exp. Biol. 35(8):801-09, 1997; Margalit, Crit. Rev. Ther. Drug Carrier Syst. 12(2-3):233-61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev. Ind. Pharm. 24(12): 1113-28, 1998). To avoid side effects due to intracellular polymeric overloading, such ultrafine particles (sized around 0.1 um) may be designed using polymers able to be degraded in vivo. Such particles can be made as described, for example, by Couvreur et al., Crit. Rev. Ther. Drug Carrier Syst. 5(1):1-20, 1988; zur Muhlen et al., Eur. J. Pharm. Biopharm. 45(2):149-55, 1998; Zambaux et al., J Controlled Release 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 200 mg/kg of body weight. However, as will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

5. Therapeutic Uses of ActRIIA Binding Agents

In certain embodiments, ActRIIA binding agents of the present invention can be used for treating or preventing a disease or condition that is associated with abnormal activity of ActRIIA and/or an ActRIIA ligand (e.g., activin A, GDF8, or GDF11). These diseases, disorders or conditions are generally referred to herein as "ActRIIA-associated conditions." In certain embodiments, the present invention provides methods of treating or preventing a disease, disorder, or condition in an individual in need thereof through administering to the individual a therapeutically effective amount of an ActRIIA binding agent as described above. These methods are particularly aimed at therapeutic and prophylactic treatments of animals, and more particularly, humans.

The present disclosure provides methods and compositions for treating conditions or disorders in an individual in need thereof by administering to the individual a therapeutically effective amount of an ActRIIA binding agent, such as, for example, a neutralizing antibody directed against ActRIIA. Mice genetically deficient in the inhibin-alpha subunit are deficient in inhibin A and inhibin B, leading to gonadal tumors that overexpress activins A and B (Matzuk et al., 1992, Nature 360:313-319; Matzuk et al., 1994, Proc Natl Acad Sci USA 91:8817-8821). All such mice develop these tumors and eventually die of a cancer cachexia-like syndrome mediated by high levels of tumor-derived activin acting through ActRIIA (Coerver et al., 1996, Mol Endocrinol 10:534-543). While not wishing to limit the invention, a neutralizing antibody directed against ActRIIA is useful for treating effects of activin-producing tumors, alleviating activin-mediated cachexia, and prolonging patient survival, as shown herein for inhibin-deficient mice (see Examples).

ActRIIA and ActRIIA-ligand complexes play essential roles in tissue growth as well as early developmental processes such as the correct formation of various structures or in one or more post-developmental capacities including sexual development, pituitary hormone production, and creation of bone and cartilage. Thus, ActRIIA-associated conditions include abnormal tissue growth and developmental defects. In addition, ActRIIA-associated conditions include, but are not limited to, disorders of cell growth and differentiation such as inflammation, allergy, autoimmune diseases, infectious diseases, and tumors.

Exemplary ActRIIA-associated conditions include neuromuscular disorders (e.g., muscular dystrophy and muscle atrophy), congestive obstructive pulmonary disease or pulmonary emphysema (and associated muscle wasting), muscle wasting syndrome, sarcopenia, cachexia, adipose tissue disorders (e.g., obesity), type 2 diabetes, and bone degenerative disease (e.g., osteoporosis). Other exemplary ActRIIA-associated conditions include musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, ActRIIA binding agents of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject ActRIIA binding agents include: Duchenne muscular dystrophy (DMD), Becker muscular dystrophy (BMD), Emery-Dreifuss muscular dystrophy (EDMD), limb-girdle muscular dystrophy (LGMD), fascioscapulohumeral muscular dystrophy (FSH or FSHD) (also known as Landouzy-Dejerine), myotonic muscular dystrophy (MMD) (also known as Steinert's Disease), oculopharyngeal muscular dystrophy (OPMD), distal muscular dystrophy (DD), congenital muscular dystrophy (CMD), and scapulohumeral muscular dystrophy (SMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, studies demonstrate that blocking or eliminating function of GDF8 (an ActRIIA ligand) in vivo can effectively treat at least certain symptoms in DMD and BMD patients. Thus, the subject ActRIIA binding agents may act as GDF8 inhibitors (antagonists), and constitute an alternative means of blocking the functions of GDF8 and/or ActRIIA in vivo in DMD and BMD patients.

In other embodiments, ActRIIA binding agents may also be used to treat or prevent muscular atrophy due to myopathies, examples of which include inflammatory myopathy, metabolic myopathy, and myotonia. Subject ActRIIA binding agents have application in treating congenital myopathies such as myotubular myopathy, nemalene myopathy, and mitochondrial myopathy. The subject ActRIIA binding agents may be used to treat inclusion body myositis, myoglobinurias, rhabdomyolysis, myositis ossificans, polymyositis, or dermatomyositis. In addition, ActRIIA binding agents may treat or prevent muscle atrophy arising from glucocorticoid treatment, sarcopenia, prolonged bed rest, skeletal immobilization, sepsis, or congestive heart failure.

The subject ActRIIA binding agents provide an effective means to increase muscle mass in other neuromuscular diseases or conditions that are in need of muscle growth. For example, amyotrophic lateral sclerosis (ALS, also known as Lou Gehrig's disease or motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move cannot reach the muscles. Most people who develop ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset. Other neuromuscular diseases in which ActRIIA binding agents may be useful include paralysis due to spinal cord injury or stroke; denervation due to trauma or degenerative, metabolic, or inflammatory neuropathy; adult motor neuron disease; autoimmune motor neuropathy with multifocal conductor block; and infantile or juvenile spinal muscular atrophy.

Increased muscle mass induced by ActRIIA binding agents might also benefit those suffering from muscle wasting diseases. Gonzalez-Cadavid et al. (1998, Proc. Natl. Acad. Sci. USA 95:14938-43) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia is generally suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., 2002, Science 296:1486-1488), the subject ActRIIA binding agents as pharmaceutical compositions can be beneficially used to prevent, treat, or alleviate the symptoms of the cachexia syndrome, where muscle growth is desired. This would include cachexia associated with cancer as well as cachexia associated with rheumatoid arthritis.

In certain embodiments, the present invention provides methods of decreasing or inhibiting FSH secretion in an individual in need thereof by administering to the individual a therapeutically effective amount of an ActRIIA binding agent, such as, for example, a neutralizing antibody directed against ActRIIA. Normal values for FSH in men range from 2-18 mIU/ml of blood. Normal values for women range from 5 and 25 mIU/mL. Levels higher than 50 mIU/mL in healthy women are associated with menopause. The tissue concentration of FSH can be determined by testing saliva (eMHP™).

In certain embodiments, the present invention provides methods of treating or preventing prostate cancer in an individual in need thereof by administering to the individual a therapeutically effective amount of an ActRIIA binding agent, such as, for example, a neutralizing antibody against ActRIIA in order to decrease or inhibit FSH secretion. These methods may be used for therapeutic as well as prophylactic treatment of humans, particularly males, who have a high risk for developing prostate cancer. As every man is at risk for developing prostate cancer, a man with a high risk for developing prostate cancer is one whose risk factors confer a greater probability of developing the disease compared to the general population or the population of men within a certain age group. Exemplary risk factors include age, family history or genetic makeup, lifestyle habits such as exercise and diet, and exposure to radiation or other cancer-causing agents.

The term "treating prostate cancer" refers to an improvement of one or more symptoms or characteristics of the disease relative to an untreated control or relative to the severity of disease prior to treatment. The term does not necessarily require that the patient receiving the treatment be cured or that the disease be completely eradicated from the patient. An agent that treats prostate cancer may be an agent that reduces the severity of one or more symptoms or characteristics of the disease. It should be noted that tumor growth and progression is influenced by a variety of factors, including mediators of cell cycle progression and cell division and regulators of cell death, or apoptosis. Accordingly, treating prostate cancer may involve a decrease in cancer cell proliferation or a decrease in the rate of cell division. Alternatively or additionally, treating prostate cancer may involve a decrease in cancer cell survival or an increase in apoptosis. Accordingly, in certain embodiments, treating prostate cancer may involve both a decrease in cell division and an increase in cell death. Regardless of mechanism, the effectiveness of an agent in treating prostate cancer may be determined by observable metrics, such as a lower number of cancer cells compared to a control (either due to decreased proliferation, increased apoptosis, or both), or a decrease in tumor size compared to a control. Therefore treating prostate cancer or inhibiting tumor or cancer cell growth is intended to be neutral as to the mechanism by which such a change occurs. Both prevention and treatment may be discerned in the diagnosis provided by a physician or other health care provider and the analysis of the intended result of administration of the therapeutic agent.

When observing the effects of the subject antagonists on prostate cancer progression in humans, an effect may be evaluated by a decrease or disappearance of measurable disease, and/or the absence of new lesions or the prevention of metastases. For example, ActRIIA binding agents may significantly reduce or delay prostate cancer progression in patients with both noninvasive and invasive prostate cancer. In addition, said agents may prevent or reduce the risk of developing prostate cancer in healthy men with risk factors for the disease. These agents may also reduce the risk of prostate cancer recurrence in patients with a history of the disease.

Accordingly, ActRIIA binding agents may be used to prevent or delay the onset of prostate cancer in individuals considered to be at risk for developing the disease, and such antagonists may be used in selected patient populations. Examples of appropriate patient populations include patients with a family history of prostate cancer, such as male patients where a father or brother has been diagnosed with the disease. In one embodiment, a patient considered to be at high risk for developing prostate cancer but who has not been diagnosed with the disease is treated with an ActRIIA binding agent. Such treatment may begin when the patient reaches the age of 30, 40, 50, 60, or 70.

ActRIIA binding agents disclosed herein, and particularly anti-ActRIIA antibodies, may be used to treat or prevent prostate cancer in a patient, including patients with solid tumors as well as patients with metastatic cancer. ActRIIA binding agents may also be administered to human subjects with precancerous or benign lesions of the prostate or with any abnormal proliferative lesions including typical hyperplasia, atypical hyperplasia, and noninvasive or in situ carcinoma. The antagonists of the present disclosure are also useful in the treatment or prevention of both hormone-dependent or hormone-responsive cancers and hormone-independent cancers (e.g., hormone-refractory prostate cancer). ActRIIA binding agents may prove to be particularly useful in tumors that express elevated (relative to normal prostate tissue-derived cells) levels of activin (e.g., A, AB or B) or elevated levels of ActRIIA.

In certain embodiments, the present invention provides methods of decreasing or inhibiting FSH secretion in an individual afflicted with an FSH-secreting pituitary tumor by administering to the individual a therapeutically effective amount of an ActRIIA binding agent, such as, for example, an anti-ActRIIA antibody. Inhibiting the hyper-secretion of FSH in these pituitary tumors is useful as a treatment to reduce the tumor symptoms, such as increased estrogen levels and the development of ovarian cysts. The present methods are preferably used in conjunction with conventional cancer therapies, such as surgery, however, the inhibition of FSH secretion alone may be an effective treatment, especially in cases where surgery or radiation is contraindicated. An anti-ActRIIA antibody may also be used to treat patients having ovarian hyperstimulation syndrome.

The present invention recognizes that the effectiveness of conventional cancer therapies (e.g., chemotherapy, radiation therapy, phototherapy, immunotherapy, and surgery, in particular prostatectomy) can be enhanced through the use of the subject binding agents. Accordingly, ActRIIA binding agents may be used in combination therapies for the treatment, prevention, or management of prostate cancer. The binding agents may be administered to patients in combination with radiation and/or surgical treatment as well as with cytotoxic chemotherapy and/or endocrine therapies. Such combination treatments may work synergistically and allow reduction of dosage of each of the individual treatments, thereby reducing the detrimental side effects exerted by each treatment at higher dosages. In other instances, malignancies that are refractory to a treatment may respond to a combination therapy of two or more different treatments. Accordingly, the disclosure relates to the administration of an ActRIIA binding agent in combination with another conventional anti-neoplastic agent, either concomitantly or sequentially, in order to enhance the therapeutic effect of the anti-neoplastic agent or overcome cellular resistance to such anti-neoplastic agent. The disclosure also relates to the administration of an ActRIIA binding agent in combination with hormonal therapy. ActRIIA binding agents may also be used in combination therapies to reduce the symptoms arising from FSH secreting pituitary tumors. Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory therapy include anti-angiogenesis agents such as (1) inhibitors of release of "angiogenic molecules," such as VEGF or bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin αvβ3, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the therapeutic ActRIIA binding agents of the invention may be continued while the other therapy is being administered and/or thereafter. Administration of the binding agents described herein may be made in a single dose, or in multiple doses. In some instances, administration of the binding agent is commenced at least several days prior to the conventional therapy, while in other instances, administration is begun either immediately before or at the time of the administration of the conventional therapy.

One aspect of the application provides for methods and compositions useful in fertility. Decreasing or inhibiting FSH secretion through the administration of an ActRIIA binding agent is a useful method to inhibit sperm maturation. In females, a decrease of FSH acts to limit proliferation of follicular granulosa cells in the ovary. Decreasing or inhibiting FSH secretion through the administration of an ActRIIA binding agent is a useful method of contraception. Reduced FSH may also delay the maturation of follicles within the ovary, thereby postponing the maturation of a limited number of follicles in women. Such treatments have the potential for increasing the possibility of natural fertilization and pregnancy later in life. Delaying maturation of follicles within the ovary by decreasing FSH secretion is also useful in preventing the depletion of oocytes, a common side effect of chemotherapy or similar treatments designed to treat rapidly dividing cells.

The present application also provides for novel compositions comprising one or more ActRIIA binding agents in combination with one or more contraceptive agents. Exemplary contraceptive agents include estrogen, progestogen, progestin (e.g., norethynodrel, norethindrone, norgestimate, norgestrel, levonorgestrel, medroxyprogesteroneand desogestrel), Ormeloxifene (Centchroman).

In certain embodiments, the present invention provides methods of treating or preventing estrogen related disorders in an individual in need thereof by administering to the individual a therapeutically effective amount of an ActRIIA binding agent, such as, for example, a neutralizing antibody directed against ActRIIA, in order to decrease or inhibit FSH secretion. Because of the controlling function of FSH on estrogen synthesis, the reduction of FSH secretion may also be effective in the treatment of estrogen related disorders such as uterine fibroids, endometriosis, polycystic ovarian disease, dysfunctional uterine bleeding, and ovarian cancer.

EXEMPLIFICATION

The invention now being generally described, it will be more readily understood by reference to the following examples, which are included merely for purposes of illustration of certain embodiments of the present invention, and are not intended to limit the invention.

Example 1

Generation of Monoclonal Antibodies

Antibodies against ActRIIA (ACVR2A) have been difficult to generate due to the high sequence conservation of this receptor among species. Applicants subjected A/J, BALB/c, and Swiss Webster strains of mice to intensive immunization protocols with different ActRIIA-based immunogens, but these attempts all failed to generate antibody.

To overcome this difficulty, Applicants used a human ActRIIA antigen construct to immunize mice possessing a null mutation in the ActRIIA gene. Acvr2a$^{-/-}$ mice (C57BL/6Acvr2a$^{tm1Zuk}$) have reduced viability, with 20-30% of mice dying perinatally due to craniofacial abnormalities (Matzuk et al., 1995, Nature 374:356-360). Homozygous males are fertile, while homozygous females are infertile. Importantly, enough Acvr2a$^{-/-}$ mice survive to adulthood to permit them to be used for the generation of monoclonal antibodies against the human ActRIIA receptor. Therefore, eight male and eight female Acvr2a$^{-/-}$ mice were immunized subcutaneously (25 µg/mouse) with the following human ActRIIA-His sequence conjugated to either keyhole limpet hemocyanin (KLH) or ovalbumin (OVA) and in the presence of complete Freund's adjuvant, incomplete Freund's adjuvant, or phosphate-buffered saline.

(SEQ ID NO: 3)
SGAILGRSETQECLFFNANWEKDRTNQTGVEPCYGDKDKRRHCFATWKN

ISGSIEIVKQGCWLDDINCYDRTDCVEKKDSPEVYFCCCEGNMCNEKFS

YFPEMEVTQPTSNPVTPKPPHHHHHH*

Blood was collected approximately 10 days after immunization to determine titers of anti-ActRIIA antibodies by indirect ELISA using ActRIIA-Fc as antigen. Based on that screening, one immunized Acvr2a$^{-/-}$ mouse received a second administration (i.p.) of ActRIIA-His-KLH (50 µg/mouse) along with anti-CD40 monoclonal antibody (10 µg/mouse), a CD40 agonist, to promote B-cell activation. Three days later, the spleen was removed, and B cells were fused with SP2/0 mouse myeloma cells by standard methods to obtain hybridomas. Promising hybridoma clones were identified based on screening for overall binding properties (ELISA), off-rate (BIACORE™ assay), and neutralization potential (cell-based reporter-gene assay). After two rounds of hybridoma subcloning, the antibody candidate 14E1.H8.H1 (Ab-14E1) was selected for sequencing, purification, and further characterization.

Example 2

Ab-14E1 Sequences

To analyze the structure of antibodies produced in accordance with the invention, nucleic acids were cloned that encode heavy and light chain variable regions from hybridomas producing anti-ActRIIA monoclonal antibodies. Messenger RNA was prepared from approximately 4×10$^6$ cells per hybridoma with a QIAshredder (Qiagen) homogenization system and an RNeasy Plus Mini Kit (Qiagen). An Advantage RT PCR Kit (Clontech) was used to synthesize first-strand cDNA, which was then used in combination with an Advantage-HF 2 PCR Kit (Clontech) and degenerate primer sets (see Zhou et al., 1994, Nucl Acids Res 22:888) to perform PCR amplification.

PCR reaction products were purified by agarose gel and a QIAquick Gel Extraction Kit (Qiagen). Sequences were then determined by standard methods using a 3' PCR primer complementary to the constant region. The VH and VL amino acid sequences for Ab-14E1 are shown in FIGS. 1 and 2, respectively, and the corresponding nucleotide sequences are shown in FIGS. 3 and 4. Note that four nucleotide substitutions were introduced near the N-terminus of VH during cloning by degenerate PCR primer, which resulted nevertheless in an active antibody. These nucleotides were adjusted in the final sequence (SEQ ID NO. 14, positions 3, 6, 7, and 12; FIG. 3) to conform to a known immunoglobulin framework sequence, as confirmed by N-terminal sequencing of purified protein from the hybridoma. Note also that silent nucleotide substitutions were introduced near the C-termini of VH (SEQ ID NO: 14, positions 351 and 357; FIG. 3) and VL (SEQ ID NO: 15; positions 312 and 315; FIG. 4) to create restriction sites for cloning.

Listed below are CDR sequences for Ab-14E1, defined according to Kabat et al. (1987, Sequences of proteins of Immunological Interest, U.S. Department of Health and Human Services, NIH, USA) and Chothia and co-workers (Al-Lazikani et al., 1997, J Mol Biol 273:927-948).

```
CDR-H1 YSITSGYYWN         (SEQ ID NO: 4)

CDR-H2 YISYDGSNNYNPSLIN   (SEQ ID NO: 5)

CDR-H3 YAYRNDVRFAY        (SEQ ID NO: 6)

CDR-L1 RASQDISNFLN        (SEQ ID NO: 7)

CDR-L2 FTSRLHS            (SEQ ID NO: 8)

CDR-L3 QQGNTLPWT          (SEQ ID NO: 9)
```

Purification of antibody protein from hybridoma conditioned medium was achieved by protein A chromatography, dialysis, viral filtration, and buffer exchange.

The N-termini of purified VH and VL proteins were confirmed by N-terminal sequencing to be

```
DVQLQESSGPG               (SEQ ID NO: 10)
and

DIQMTQTTS,                (SEQ ID NO: 11)
``` respectively.

Example 3

Sites of Contact Between Ab-14E1 and ActRIIA

To identify specificity-determining residues (SDRs) in Ab-14E1, sites of contact between Ab-14E1 and human ActRIIA were located by x-ray crystallographic analysis of a) 14E1 Fab alone and b) 14E1 Fab complexed with ActRIIA extracellular domain (ECD).

Protein Generation.

14E1 Fab was prepared for crystallization by digesting Ab-14E1 with activated papain at a ratio of 100:1 (w/w) Ab-14E1:papain in phosphate-buffered saline containing 4 mM EDTA and 10 mM cysteine for 4 h at 37° C. The digested sample was diluted two-fold, adjusted to pH 9.5, and subjected to chromatography with HiTrap Q Sepharose™ (GE Healthcare) to separate the Fab component (flow-through), which was then purified further with size-exclusion chromatography. Purified 14E1 Fab was stored at 12 mg/ml in a solution containing 5 mM Tris (pH 8.0), 25 mM NaCl, and 2 mM EDTA.

ActRIIA ECD was prepared for crystallization from a fusion protein consisting of human ActRIIA ECD attached to an Fc domain by a linker containing an enterokinase cleavage site. ActRIIA ECD was obtained by digestion of this fusion protein with enterokinase overnight at 37° C. and removal of the Fc component with MABSELECT™ (GE Healthcare) chromatography. ActRIIA ECD was then deglycosylated with Endoglycosidase $H_f$ (New England Biolabs), purified with size-exclusion chromatography, digested with carboxypeptidases B and Y (ratio of 20:1 ActRIIA ECD: CPB/CPY in phosphate-buffered saline, incubated overnight at 37° C.), and purified again with size-exclusion chromatography. To generate the protein complex, purified 14E1 Fab was mixed with purified ActRIIA ECD in a ratio of 1:1.2 and purified a final time with size-exclusion chromatography. The purified complex of 14E1 Fab and ActRIIA ECD was stored at 20.5 mg/ml in a solution containing 10 mM Tris (pH 8.0) and 25 mM sodium chloride.

Crystallization Methods.

14E1 Fab was crystallized in conditions containing polyethylene glycols at 15-25%, salts such as potassium thiocyanate, sodium sulfate, malonate, or potassium sodium tartrate, and at pH values ranging from 5.5 to 8.5. Data was collected from crystals grown in 20% polyethylene glycol 3350, 200 mM sodium sulfate, and 100 mM bis-tris propane, at pH 7.75. These crystals were transferred into buffer consisting of crystallization buffer and glycerol in a ratio of 3:1 (v/v) and flash frozen in liquid nitrogen before transfer onto the x-ray system.

The complex of 14E1 Fab and ActRIIA ECD was crystallized in conditions containing polyethylene glycols at 7-15%, zinc chloride at 1-15 mM, and at pH values between 5.5 and 7.5. Data was collected from crystals grown in 8% polyethylene glycol 8000, 8 mM zinc chloride, and 100 mM HEPES, at pH 7.00. These crystals were transferred into crystallization buffer containing 25% ethylene glycol and flash frozen in liquid nitrogen before transfer onto the x-ray system.

Crystallographic Data

The following crystallographic data were obtained for 14E1 Fab and the complex of 14E1 Fab with ActRIIA ECD.

|  | 14E1 Fab | 14E1 Fab/ActRIIA ECD |
| --- | --- | --- |
| Space group | $P4_12_12$ | $I2_12_12_1$ |
| Cell dimensions |  |  |
| a, b, c (Å) | 107.30, 107.30, 96.53 | 75.47, 91.79, 140.61 |
| α, β, γ (°) | 90.00, 90.00, 90.00 | 90.00, 90.00, 90.00 |
| Resolution (Å) | 1.90 (1.93-1.90) | 2.91 (2.96-2.91) |
| $R_{merge}$ | 0.051 (0.309) | 0.037 (0.171) |
| I/σI | 38.2 (5.0) | 24.7 (4.6) |
| Completeness (%) | 99.8 (98.0) | 91.0 (67.7) |
| Redundancy | 7.6 (3.3) | 3.4 (3.0) |
| Refinement |  |  |
| Resolution (Å) | 1.90 | 2.95 |
| $R_{work}/R_{free}$ | 0.178/0.219 | 0.207/0.288 |
| No. atoms/B-Factor | 3668/25.44 | 4074/53.8 |
| Protein | 3296/24.34 | 4028/52.61 |
| Water | 372/35.28 | 46/32.2 |
| R.m.s deviations |  |  |
| Bond lengths (Å) | 0.006 | 0.004 |
| Bond angles (°) | 1.061 | 0.847 |

Structural Refinement Process.

To determine the crystal structure of 14E1 Fab, applicants used PDB structure 1FIG as a model for molecular replacement modeling and obtained a single solution consisting of one Fab molecule, as expected. Homologous VL and VH domains from PDB structures 2A6D and 1KEN, respectively, were superimposed onto corresponding 1FIG domains. Positioned VL and VH domains were replaced to generate a new 14E1 Fab model, which was refined through adjustment of conflicting sequence areas. The 14E1 Fab model was rebuilt and further refined with these adjusted sequences to yield an excellent model as evaluated by final statistics (see above table).

To determine the crystal structure of the complex between 14E1 Fab and ActRIIA ECD, applicants used the 14E1 structure and PDG 2GOO structures of ActRIIA as models for molecular replacement. As expected, a single solution consisting of one ActRIIA molecule and one 14E1 Fab molecule was obtained. The 14E1 Fab and ActRIIA ECD models were then rebuilt and refined to yield a good-quality model as evaluated by final statistics (see above table).

Structural Results.

Crystallographic analysis revealed a large contact surface (total buried surface area approximately 2650 Å$^2$) between 14E1 Fab and ActRIIA ECD overlapping extensively with the previously determined ligand binding region on ActRIIA (Greenwald et al., 1999, Nat Struct Biol 6:18-22; Gray et al., 2000, J Biol Chem 275:3206-3212; Allendorph et al., 2006, Proc Natl Acad Sci USA 103:7643-7648). Specific amino acid residues in 14E1 Fab VH that contact ActRIIA, as determined with by software analysis (Acta Cryst D50:760-763, 1994), are shown in FIG. 5 and also listed in the table below along with the number of atomic contacts that each VH residue makes with individual ActRIIA residues. In the table below, amino acid positions in VH are defined with respect to three alternative reference points: a) the N-terminal aspartate residue; b) the first cysteine residue (C1, position 22) redefined as position 0; or c) the second cysteine residue (C2, position 96) redefined as position 0. Numbering of ActRIIA ECD residues in the table below is the same as in FIG. 6, which shows the distribution of VH-contacted ActRIIA residues within the ActRIIA ECD sequence (SEQ ID NO: 16).

| 14E1 Fab VH Residue | | | | | |
|---|---|---|---|---|---|
| | | Position | | ActRIIA | Number |
| Amino Acid | N-term = 1 | 1$^{st}$ Cys = 0 | 2$^{nd}$ Cys = 0 | ECD Residue | of Atomic Contacts |
| Val | 2 | −20 | −94 | Asp 34 | 11 |
| | | | | Asp 36 | 1 |
| Gly | 26 | 4 | −70 | Asp 34 | 5 |
| Tyr | 27 | 5 | −69 | Tyr 32 | 7 |
| | | | | Gly 33 | 21 |
| | | | | Asp 34 | 25 |
| Ser | 31 | 9 | −65 | Tyr 32 | 13 |
| Gly | 32 | 10 | −64 | Tyr 32 | 10 |
| Tyr | 33 | 11 | −63 | Tyr 32 | 6 |
| | | | | Gly 33 | 13 |
| | | | | Asp 34 | 19 |
| | | | | Lys 37 | 1 |
| | | | | Leu 61 | 2 |
| Tyr | 34 | 12 | −62 | Glu 29 | 2 |
| Tyr | 54 | 32 | −42 | Pro 30 | 4 |
| | | | | Tyr 32 | 14 |
| Asn | 59 | 37 | −37 | Asp 21 | 1 |
| | | | | Arg 22 | 3 |
| Ala | 100 | 78 | 4 | Tyr 32 | 1 |
| | | | | Leu 61 | 4 |
| Tyr | 101 | 79 | 5 | Glu 29 | 12 |
| | | | | Pro 30 | 2 |
| | | | | Cys 31 | 20 |
| | | | | Tyr 32 | 13 |
| | | | | Gly 33 | 2 |
| | | | | Arg 39 | 9 |
| | | | | His 40 | 1 |
| | | | | Cys 59 | 34 |
| | | | | Trp 60 | 13 |
| | | | | Leu 61 | 12 |
| Arg | 102 | 80 | 6 | Phe 13 | 8 |
| | | | | Arg 22 | 2 |
| | | | | Thr 23 | 9 |
| | | | | Glu 29 | 11 |
| Asn | 103 | 81 | 7 | Phe 13 | 15 |
| | | | | Phe 14 | 7 |
| | | | | Asn 15 | 15 |
| | | | | Asp 21 | 1 |
| | | | | Glu 29 | 2 |
| | | | | Phe 42 | 10 |
| | | | | Lys 56 | 30 |
| | | | | Gln 57 | 13 |
| | | | | Gly 58 | 3 |
| | | | | Trp 60 | 2 |
| Asp | 104 | 82 | 8 | Phe 42 | 1 |
| | | | | Cys 59 | 6 |
| | | | | Trp 60 | 22 |
| | | | | Leu 61 | 11 |
| Arg | 106 | 84 | 10 | Trp 60 | 15 |
| | | | | Leu 61 | 27 |
| | | | | Asp 62 | 10 |
| | | | | Asp 63 | 4 |
| Ala | 108 | 86 | 12 | Leu 61 | 1 |
| Tyr | 109 | 87 | 13 | Asp 34 | 6 |
| | | | | Lys 37 | 8 |

The specific amino acid residues in 14E1 Fab VL that contact ActRIIA are shown in FIG. 7 and also listed in the table below along with the number of atomic contacts that each VL residue makes with individual ActRIIA residues. In the table below, amino acid positions in VL are defined with respect to three alternative reference points: a) the N-terminal aspartate residue; b) the first cysteine residue (C1, position 23) redefined as position 0; or c) the second cysteine residue (C2, position 88) redefined as position 0. Numbering of ActRIIA ECD residues in the table below is the same as in FIG. 8, which shows the distribution of VL-contacted ActRIIA residues within the ActRIIA ECD sequence (SEQ ID NO: 16).

| 14E1 Fab VL Residue | | | | | |
|---|---|---|---|---|---|
| | | Position | | ActRIIA | Number |
| Amino Acid | N-term = 1 | 1$^{st}$ Cys = 0 | 2$^{nd}$ Cys = 0 | ECD Residue | of Atomic Contacts |
| Asp | 28 | 5 | −60 | Lys 46 | 4 |
| Ser | 30 | 7 | −58 | Lys 46 | 4 |
| | | | | Val 55 | 3 |
| | | | | Val 81 | 11 |
| Asn | 31 | 8 | −57 | Glu 80 | 1 |
| | | | | Val 81 | 9 |

-continued

| 14E1 Fab VL Residue | | | | ActRIIA ECD Residue | Number of Atomic Contacts |
|---|---|---|---|---|---|
| Amino Acid | Position N-term = 1 | 1st Cys = 0 | 2nd Cys = 0 | | |
| Phe | 32 | 9 | −56 | Phe 42 | 4 |
| | | | | Thr 44 | 9 |
| | | | | Val 55 | 3 |
| | | | | Lys 56 | 19 |
| | | | | Typ 60 | 1 |
| Tyr | 49 | 26 | −39 | Trp 60 | 6 |
| | | | | Asp 62 | 3 |
| | | | | Asp 63 | 17 |
| | | | | Ile 64 | 4 |
| Phe | 50 | 27 | −38 | Thr 44 | 3 |
| | | | | Trp 60 | 6 |
| | | | | Val 81 | 3 |
| | | | | Phe 83 | 21 |
| Ser | 52 | 29 | −36 | Lys 76 | 1 |
| Arg | 53 | 30 | −35 | Trp 60 | 2 |
| | | | | Asp 63 | 14 |
| | | | | Asn 65 | 17 |
| | | | | Cys 66 | 1 |
| | | | | Lys 76 | 1 |
| | | | | Phe 83 | 21 |
| | | | | Cys 85 | 1 |
| Leu | 54 | 31 | −34 | Ile 64 | 2 |
| Ser | 56 | 33 | −32 | Lys 37 | 2 |
| Ser | 67 | 44 | −21 | Glu 80 | 1 |
| Gly | 91 | 68 | 3 | Lys 56 | 4 |
| Asn | 92 | 69 | 4 | Asn 17 | 13 |
| | | | | Asp 21 | 5 |
| | | | | Lys 56 | 10 |
| Thr | 93 | 70 | 5 | Asn 17 | 6 |
| | | | | *Arg 20 | 4 |
| | | | | Asp 21 | 11 |
| | | | | Lys 56 | 1 |
| Leu | 94 | 71 | 6 | *Arg 20 | 13 |
| | | | | Asp 21 | 12 |
| Trp | 96 | 73 | 8 | Asp 21 | 5 |

*The ActRIIA structure (PDB structure 2GOO) used for modeling the 14E1-ActRIIA complex is based on a murine sequence with a conservative substitution (Lys to Arg) at ECD position 20 compared with the human sequence (SEQ ID NO: 16); however, the side chain of either residue is disordered and does not appreciably affect the overall structure of the complex.

Example 4

ActRIIA Binding and Neutralization by Ab-14E1

Figure 9:
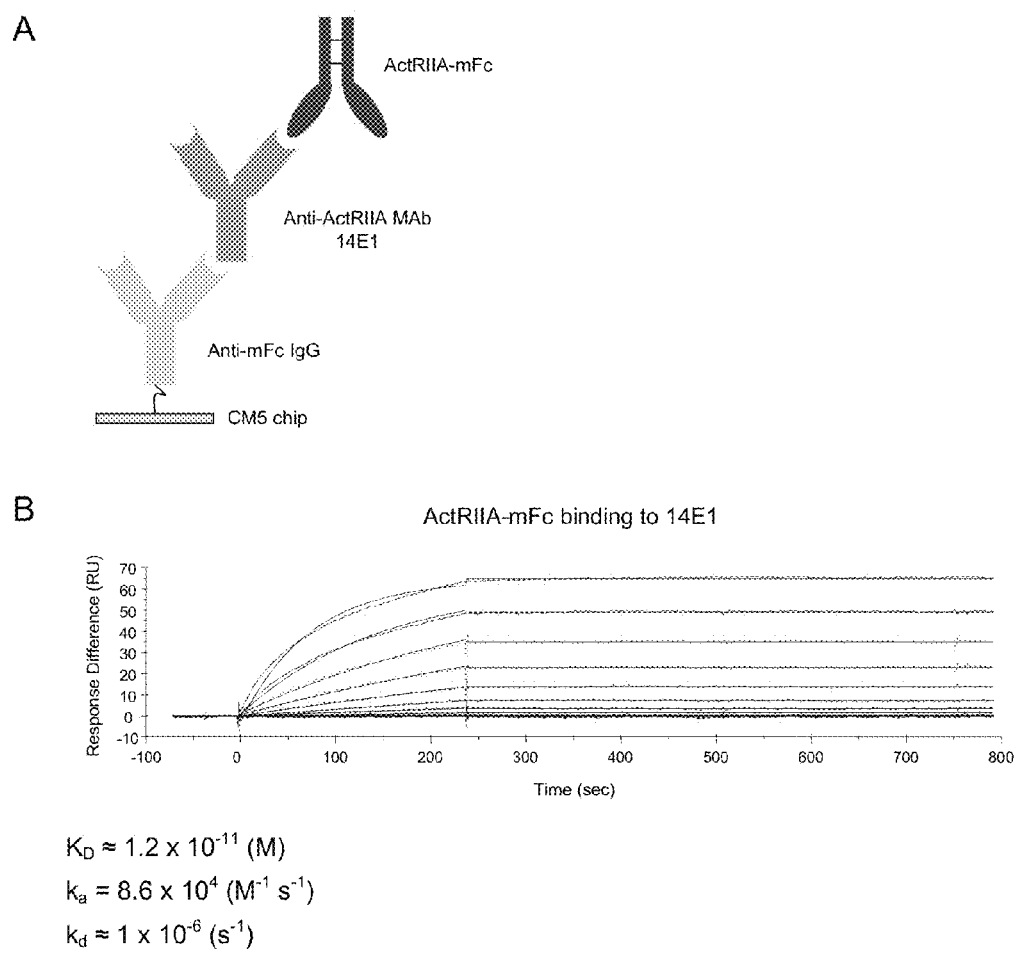
FIG. 9 depicts the kinetics of ActRIIA-Fc binding to Ab-14E1 as determined by BIACORE™-based analysis. A. Ab-14E1 was captured on a chip with covalently immobilized anti-mFC IgG and then exposed to ActRIIA-Fc at different concentrations. B. Analysis by nonlinear regression yielded a $K_D$ of 12 pM, which is approximate since the dissociation rate constant ($k_d$, $10^{-6}$ $s^{-1}$) from which it is calculated was too slow to be measured accurately. RU, relative units.

Applicants used plasmon surface resonance (BIA-CORE™-based analysis) to determine the kinetics and affinity of human ActRIIA binding by purified Ab-14E1. This antibody was found to bind ActRIIA-mFc (dimeric protein) with a $K_D$ of approximately 12 pM (FIG. 9) and to bind monomeric ActRIIA tagged with histidine (ActRIIA-His) at ten-fold lower affinity.

Figure 10:
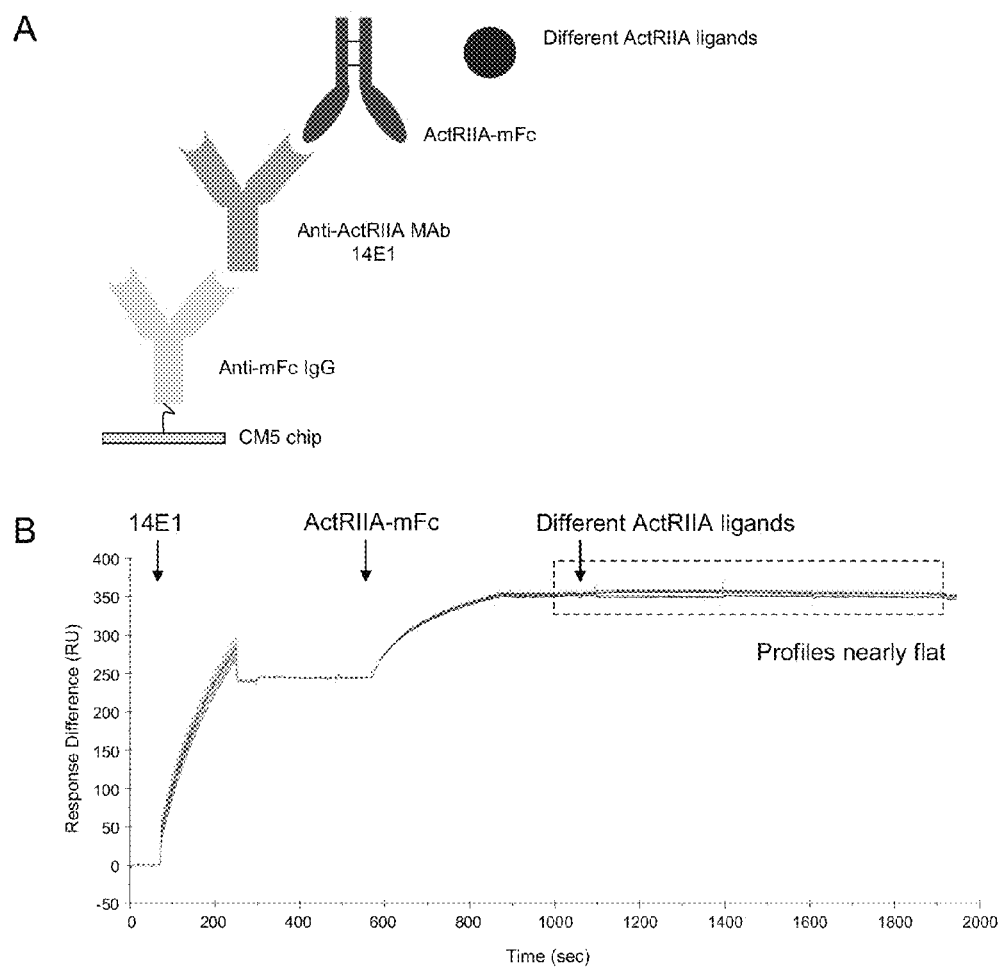
FIG. 10 depicts the ability of Ab-14E1 to block binding of ActRIIA-Fc to different ActRIIA ligands. A. In this BIACORE™-based determination, ActRIIA-Fc was first allowed to bind to captured Ab-14E1 and then exposed to activin A, activin B, activin AB, BMP-10, GDF-3, GDF-8, or GDF-11 (each at 20 nM). B. As indicated by the nearly flat response profiles, binding of these ligands to ActRIIA-Fc was almost completely inhibited by Ab-14E1.
Figure 11:
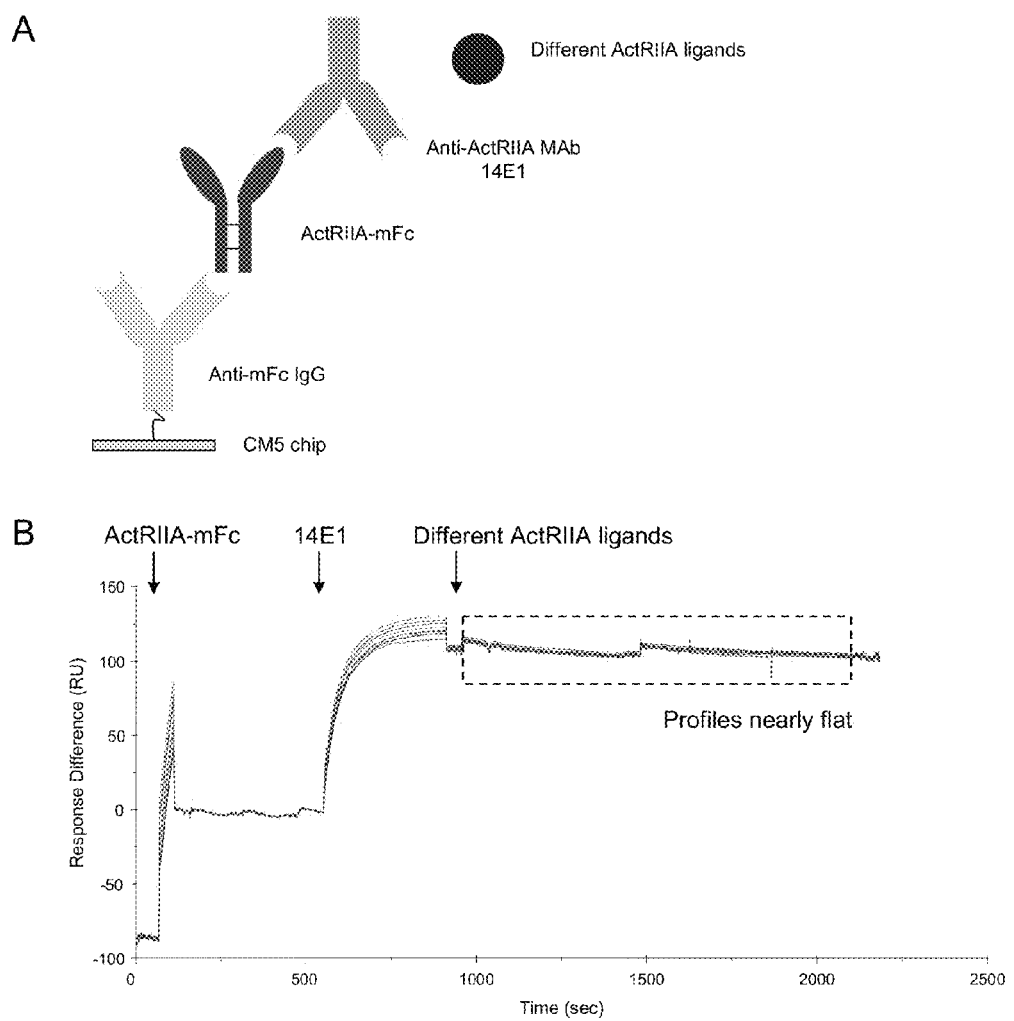
FIG. 11 depicts use of a reversed protein configuration to demonstrate the ability of Ab-14E1 to block binding of ActRIIA-Fc to different ActRIIA ligands. A. In this BIACORE™-based determination, captured ActRIIA-Fc was allowed to bind Ab-14E1 and then exposed to activin A, activin B, activin AB, BMP-10, GDF-3, GDF-8, or GDF-11 (each at 20 nM). B. As in FIG. 10, ligand binding to ActRIIA-Fc was almost completely inhibited by Ab-14E1.
Figure 12:
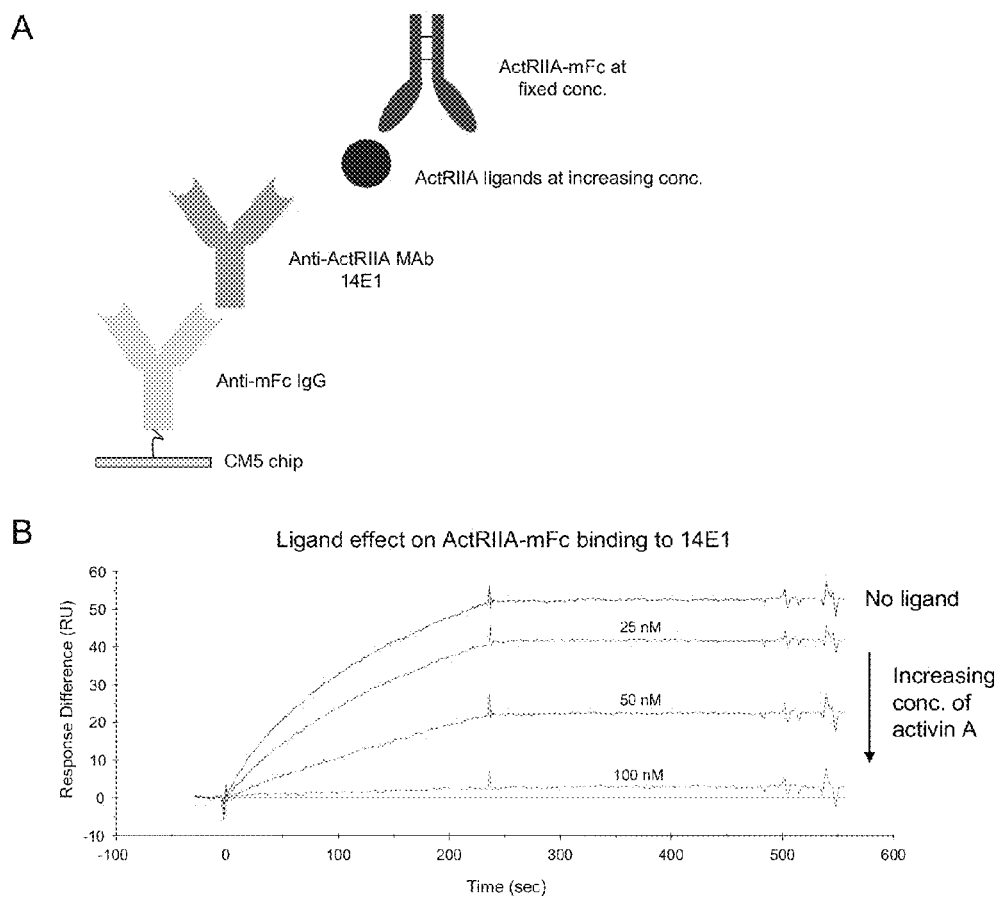
FIG. 12 depicts the ability of ActRIIA ligands to competitively inhibit binding of ActRIIA-Fc to Ab-14E1. A. In this BIACORE™-based determination, captured Ab-14E1 was exposed to solutions containing a fixed concentration of ActRIIA-Fc (50 nM) premixed with varying concentrations of a given ligand (activin A, activin B, activin AB, BMP-10, or GDF-11). B. At the highest concentration tested (100 nM), activin A (shown) and BMP-10 inhibited binding of ActRIIA-Fc to Ab-14E1 by 95%, while the other ligands displayed lesser degrees of inhibition at this concentration.

Additionally, BIACORE™-based analysis was used to determine whether Ab-14E1 can block the binding of ActRIIA to its cognate ligands. Significantly, binding of multiple ligands to ActRIIA-Fc was prevented by preincubation of ActRIIA-Fc with Ab-14E1 in two different test configurations (FIGS. 10-11), thus indicating the neutralizing capability of Ab-14E1. Similar results were obtained when dimeric ActRIIA-Fc was replaced with monomeric extracellular domain of ActRIIA tagged with histidine. Moreover, ActRIIA ligands, most notably activin A, competitively inhibited binding of Ab-14E1 to ActRIIA-Fc in a concentration-dependent manner (FIG. 12), thus providing additional evidence of ActRIIA neutralization due to shared epitopes.

Example 5

Neutralization of ActRIIA Signaling by Ab-14E1 in a Cell-Based Assay

A reporter gene assay in A204 cells was used to evaluate the effects of purified anti-ActRIIA antibody on signaling by ActRIIA ligands activin A and activin B. This assay is based on a human rhabdomyosarcoma cell line transfected with a pGL3(CAGA)12 reporter plasmid (Dennler et al, 1998, EMBO 17: 3091-3100) as well as a Renilla reporter plasmid (pRLCMV) to control for transfection efficiency. The CAGA12 motif is present in TGF-beta responsive genes (PAI-1 gene), so this vector is of general use for factors signaling through Smad2 and Smad3. Since the A204 cell line expresses primarily ActRIIA, it is suitable for testing antibodies for potential ActRIIA neutralizing ability. In the absence of such inhibitors, ActRIIA ligands can dose-dependently stimulate ActRIIA signaling in A204 cells.

On the first day of the assay, A204 cells (ATCC HTB-82) were distributed in 48-well plates at $10^5$ cells per well. On the next day, a solution containing 10 μg pGL3(CAGA)12, 1 μg pRLCMV, 30 μl Fugene 6 (Roche Diagnostics), and 970 μl OptiMEM (Invitrogen) was preincubated for 30 min, then added to McCoy's growth medium, which was applied to the plated cells (500 μl/well) for incubation overnight at room temperature. On the third day, medium was removed and cells incubated for 6 h at 37° C. with test substances (250 μl/well) diluted in phosphate-buffered saline containing 0.1% BSA. After rinsing, cells were lysed with passive lysis buffer (Promega E1941) and stored overnight at −70° C. On the fourth and final day, plates were warmed to room temperature with gentle shaking Cell lysates were transferred in duplicate to a chemoluminescence plate (96-well) and analyzed in a luminometer with reagents from a Dual-Luciferase Reporter Assay system (Promega E1980) to determine normalized luciferase activity.

Ab-14E1 was a potent inhibitor of activin A signaling in this assay (FIG. 13). Similar results were obtained for Ab-14E1 with activin B, thus indicating that Ab-14E1 can neutralize ActRIIA-mediated signaling in a cell-based system.

Example 6

Inhibitory Effect of Ab-14E1 on FSH Levels in Mice

Activin was originally identified by its ability to increase FSH secretion from pituitary gonadotropes. Activin-mediated signaling, in part through ActRIIA, is now thought to promote FSH secretion through actions at multiple regulatory levels (Gregory et al., 2004, Semin Reprod Med 22:253-267). Therefore, Applicants investigated the ability of Ab-14E1 to inhibit circulating FSH concentrations in mice as an in vivo test of the antibody's neutralizing capability. Female C57BL/6 mice (6 weeks old) underwent either a sham operation (n=16) or a bilateral ovariectomy (OVX; n=18) to disinhibit FSH secretion and thereby increase sensitivity to exogenous inhibitory factors. Mice were allowed a 6-week recovery period and then treated twice-weekly with Ab-14E1 (50 mg/kg, s.c.) or vehicle (Tris-buffered saline). Blood samples were collected after 4 weeks of treatment in the OVX mice and 8 weeks of treatment in the gonad-intact (sham) mice, and serum levels of mouse FSH were determined by radioimmunoassay. As shown in FIG. 14, treatment with Ab-14E1 reduced serum FSH concentrations by more than 50% in OVX mice (p<0.01) and by more than 30% in sham mice, although the latter difference did not reach statistical significance. The results of this study are consistent with the ability of Ab-14E1 to neutralize ActRIIA signaling in vivo.

Example 7

Effect of Ab-14E1 on Cancer Cachexia in Inhibin-Deficient Mice

Mice genetically deficient in the inhibin-alpha subunit develop gonadal tumors that overexpress activins A and B (Matzuk et al., 1992, Nature 360:313-319; Matzuk et al., 1994, Proc Natl Acad Sci USA 91:8817-8821). All such mice develop these tumors and eventually die of a cancer cachexia-like syndrome mediated by high levels of tumor-derived activin acting through ActRIIA (Coerver et al., 1996, Mol Endocrinol 10:534-543). Therefore, Applicants investigated the ability of Ab-14E1 to inhibit cachexia in these mice. Beginning at six weeks of age, male and female mice homozygous for the inhibin-alpha null allele were treated twice per week, subcutaneously, with either Ab-14E1 (10 mg/kg) or vehicle (phosphate-buffered saline). Mice were monitored daily and euthanized in the event of serious morbidity (dehydration, lethargy, hunched posture, unkempt appearance, dyspnea, or loss of greater than twenty percent of original body weight), and body weight was determined twice per week as an index of treatment effectiveness. As shown in FIG. 15, male mice treated with Ab-14E1 (n=9) displayed better weight gain over the course of the study than did vehicle-treated males (n=11), and there was a trend toward improved survival with Ab-14E1 treatment in males (data not shown). Unlike their male counterparts, vehicle-treated female mice unexpectedly failed to develop substantial cachexia, and treatment of females with Ab-14E1 resulted in only a non-significant trend toward improved body weight compared to vehicle. The results of this study indicate that Ab-14E1 can alleviate tumor-dependent cachexia in vivo caused by excess activin-ActRIIA signaling.

Taken together, the foregoing findings demonstrate that immunization of ActRIIA-deficient mice with ActRIIA antigen yielded a monoclonal antibody (Ab-14E1) capable of binding to ActRIIA with high affinity, neutralizing ActRIIA-mediated signaling in multiple assay systems of varying complexity, and alleviating activin-dependent cancer cachexia in vivo.

Example 8

Stimulatory Effect of Ab-14E1 on Muscle in Normal Mice

Applicants investigated the effect of Ab-14E1 on body weight and lean mass in normal mice. Beginning at 6 weeks of age, male C57BL/6 mice were treated with Ab-14E1 (10 mg/kg, i.p., n=10) or vehicle (phosphate-buffered saline, n=5) twice weekly for 4 weeks. Body weights were determined twice weekly, and lean mass was determined by whole-body nuclear magnetic resonance (NMR) at baseline and after 4 weeks of treatment. As shown in FIG. 16, mice treated with Ab-14E1 showed significantly greater weight gain than controls throughout the course of the study. By study end, mice treated with Ab-14E1 gained more than twice as much whole-body lean mass as controls (FIG. 17). At study end, pectoralis muscle weight (bilateral) in mice treated with Ab-14E1 was 15% greater than that in vehicle-treated mice, a difference that trended toward significance (p=0.137). In addition, there was a substantially lower accumulation of whole-body fat mass with Ab-14E1 treatment compared to vehicle (p=0.058), indicating that antibodies directed to ActRIIA can be used to decrease fat accumulation. The foregoing results demonstrate that treatment with an anti-ActRIIA antibody can increase weight gain, specifically gain in lean mass (an indicator of muscle mass), in a normal mouse.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. An isolated antibody or fragment thereof that inhibits binding of activin A to human ActRIIA, said isolated antibody or fragment thereof comprising a heavy chain complementarity determining region (CDR-H) 1, CDR-H2, and CDR-H3, and a light chain complementarity determining region (CDR-L) 1, CDR-L2, and CDR-L3 whose amino acid sequences are SEQ ID NOs: 4, 5, 6, 7, 8, and 9, respectively.

2. The isolated antibody or fragment thereof of claim 1, that binds to human ActRIIa and cross-blocks the binding of Ab-14E1 to human ActRIIA.

3. The isolated antibody or fragment thereof of claim 1, that inhibits binding of activin A and activin B to human ActRIIA.

4. The antibody or fragment thereof of claim 1 wherein said anti-ActRIIA antibody or fragment has an activity selected from the group consisting of: (a) reduces follicle-stimulating hormone levels in vivo, and (b) inhibits activin A signaling in a cell line in vitro.

5. The antibody or fragment thereof of claim 1 wherein said anti-ActRIIA antibody or fragment has an activity selected from the group consisting of: (a) reduces follicle-stimulating hormone levels in an ovariectomized, female C57BL/6 mouse, and (b) inhibits expression of a CAGA12-regulated reporter gene in an A204 cell line exposed to activin A.

6. The isolated antibody or fragment thereof of claim 1, wherein said antibody or fragment thereof contacts one or more amino acids in the extracellular domain of human ActRIIA, selected from a group consisting of:
   a. a phenylalanine at position 13 of SEQ ID NO: 16,
   b. a phenylalanine at position 14 of SEQ ID NO: 16,
   c. an asparagine at position 15 of SEQ ID NO: 16,
   d. an asparagine at position 17 of SEQ ID NO: 16,
   e. an aspartate at position 21 of SEQ ID NO: 16,
   f. an arginine at position 22 of SEQ ID NO: 16,
   g. a threonine at position 23 of SEQ ID NO: 16,
   h. a glutamate at position 29 of SEQ ID NO: 16,
   i. a proline at position 30 of SEQ ID NO: 16,
   j. a cysteine at position 31 of SEQ ID NO: 16,
   k. a tyrosine at position 32 of SEQ ID NO: 16,
   l. a glycine at position 33 of SEQ ID NO: 16,
   m. an aspartate at position 34 of SEQ ID NO: 16,
   n. an aspartate at position 36 of SEQ ID NO: 16,
   o. a lysine at position 37 of SEQ ID NO: 16,
   p. an arginine at position 39 of SEQ ID NO: 16,
   q. a histidine at position 40 of SEQ ID NO: 16,
   r. a phenylalanine at position 42 of SEQ ID NO: 16,
   s. a threonine at position 44 of SEQ ID NO: 16,
   t. a lysine at position 46 of SEQ ID NO: 16,
   u. a valine at position 55 of SEQ ID NO: 16,
   v. a lysine at position 56 of SEQ ID NO: 16,
   w. a glutamine at position 57 of SEQ ID NO: 16,
   x. a glycine at position 58 of SEQ ID NO: 16,
   y. a cysteine at position 59 of SEQ ID NO: 16,
   z. a tryptophan at position 60 of SEQ ID NO: 16,
   aa. a leucine at position 61 of SEQ ID NO: 16,
   bb. an aspartate at position 62 of SEQ ID NO: 16,
   cc. an aspartate at position 63 of SEQ ID NO: 16,
   dd. an isoleucine at position 64 of SEQ ID NO: 16,
   ee. an asparagine at position 65 of SEQ ID NO: 16,
   ff. a cysteine at position 66 of SEQ ID NO: 16,
   gg. a lysine at position 76 of SEQ ID NO: 16,
   hh. a glutamate at position 80 of SEQ ID NO: 16,
   ii. a valine at position 81 of SEQ ID NO: 16,
   jj. a phenylalanine at position 83 of SEQ ID NO: 16, and
   kk. a cysteine at position 85 of SEQ ID NO: 16.

7. The antibody or fragment thereof according to claim 1 comprising a heavy chain wherein said heavy chain comprises a polypeptide having at least 80% identity to the sequence given in SEQ ID NO: 12.

8. The antibody or fragment thereof according to claim 1 comprising a light chain wherein said light chain comprises a polypeptide having at least 80% identity to the sequence given in SEQ ID NO: 13.

9. The antibody or fragment thereof according to claim 1 comprising both a heavy chain and a light chain wherein the heavy chain comprises a polypeptide having at least 80% identity to the sequence given in SEQ ID NO: 12 and the light chain comprises a polypeptide having at least 80% identity to the sequence given in SEQ ID NO: 13.

10. A pharmaceutical composition comprising the antibody or fragment of claim 1.

11. The antibody or fragment thereof according to claim 1 in combination with one or more of a pharmaceutically acceptable excipient, diluent, or carrier.

12. The antibody or fragment thereof according to claim 1 conjugated to at least one of Fc, polyethylene glycol, albumin, and transferrin.

* * * * *

SEQUENCE LISTING

```
<160> NUMBER OF SEQ ID NOS: 18

<210> SEQ ID NO 1
<211> LENGTH: 513
<212> TYPE: PRT
<213> ORGANISM: Homo sapiens

<400> SEQUENCE: 1

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60
```

-continued

```
Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Val Glu Lys Lys Asp
             85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Tyr Tyr Asn Ile Leu Leu Tyr Ser Leu
            130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
            195                 200                 205

Ala Gln Leu Leu Asn Glu Tyr Val Ala Val Lys Ile Phe Pro Ile Gln
            210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
            275                 280                 285

Leu Cys His Ile Ala Glu Thr Met Ala Arg Gly Leu Ala Tyr Leu His
            290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
            370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
            405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
            435                 440                 445

Ala Gly Met Ala Met Leu Cys Glu Thr Ile Glu Glu Cys Trp Asp His
            450                 455                 460

Asp Ala Glu Ala Arg Leu Ser Ala Gly Cys Val Gly Glu Arg Ile Thr
465                 470                 475                 480
```

Gln Met Gln Arg Leu Thr Asn Ile Ile Thr Thr Glu Asp Ile Val Thr
            485                 490                 495

Val Val Thr Met Val Thr Asn Val Asp Phe Pro Pro Lys Glu Ser Ser
        500                 505                 510

Leu

<210> SEQ ID NO 2
<211> LENGTH: 1542
<212> TYPE: DNA
<213> ORGANISM: Homo sapiens

<400> SEQUENCE: 2

| | | | | | | |
|---|---|---|---|---|---|---|
| atgggagctg | ctgcaaagtt | ggcgtttgcc | gtctttctta | tctcctgttc | ttcaggtgct | 60 |
| atacttggta | gatcagaaac | tcaggagtgt | cttttcttta | atgctaattg | ggaaaaagac | 120 |
| agaaccaatc | aaactggtgt | tgaaccgtgt | tatggtgaca | agataaacg | gcggcattgt | 180 |
| tttgctacct | ggaagaatat | ttctggttcc | attgaaatag | tgaaacaagg | ttgttggctg | 240 |
| gatgatatca | actgctatga | caggactgat | tgtgtagaaa | aaaagacag | ccctgaagta | 300 |
| tattttttgtt | gctgtgaggg | caatatgtgt | aatgaaaagt | tttcttattt | tccagagatg | 360 |
| gaagtcacac | agcccacttc | aaatccagtt | acacctaagc | caccctatta | caacatcctg | 420 |
| ctctattcct | tggtgccact | tatgttaatt | gcggggattg | tcatttgtgc | attttgggtg | 480 |
| tacaggcatc | acaagatggc | ctaccctcct | gtacttgttc | caactcaaga | cccaggacca | 540 |
| ccccccacctt | ctccattact | agggttgaaa | ccactgcagt | tattagaagt | gaaagcaagg | 600 |
| ggaagatttg | ttgtgtctg | gaaagcccag | ttgcttaacg | aatatgtggc | tgtcaaaata | 660 |
| tttccaatac | aggacaaaca | gtcatggcaa | aatgaatacg | aagtctacag | tttgcctgga | 720 |
| atgaagcatg | agaacatatt | acagttcatt | ggtgcagaaa | aacgaggcac | cagtgttgat | 780 |
| gtggatcttt | ggctgatcac | agcatttcat | gaaaagggtt | cactatcaga | ctttcttaag | 840 |
| gctaatgtgg | tctcttggaa | tgaactgtgt | catattgcag | aaaccatggc | tagaggattg | 900 |
| gcatatttac | atgaggatat | acctggccta | aaagatggcc | acaaacctgc | catatctcac | 960 |
| agggacatca | aaagtaaaaa | tgtgctgttg | aaaaacaacc | tgacagcttg | cattgctgac | 1020 |
| tttgggttgg | ccttaaaatt | tgaggctggc | aagtctgcag | gcgataccca | tggacaggtt | 1080 |
| ggtacccgga | ggtacatggc | tccagaggta | ttagagggtg | ctataaactt | ccaagggat | 1140 |
| gcatttttga | ggatagatat | gtatgccatg | ggattagtcc | tatgggaact | ggcttctcgc | 1200 |
| tgtactgctg | cagatggacc | tgtagatgaa | tacatgttgc | catttgagga | ggaaattggc | 1260 |
| cagcatccat | ctcttgaaga | catgcaggaa | gttgttgtgc | ataaaaaaaa | gaggcctgtt | 1320 |
| ttaagagatt | attggcagaa | acatgctgga | atggcaatgc | tctgtgaaac | cattgaagaa | 1380 |
| tgttgggatc | acgacgcaga | agccaggtta | tcagctggat | gtgtaggtga | agaattacc | 1440 |
| cagatgcaga | gactaacaaa | tattattacc | acagaggaca | ttgtaacagt | ggtcacaatg | 1500 |
| gtgacaaatg | ttgactttcc | tcccaaagaa | tctagtctat | ga | | 1542 |

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 3

Ser Gly Ala Ile Leu Gly Arg Ser Glu Thr Gln Glu Cys Leu Phe Phe
1               5                   10                  15

Asn Ala Asn Trp Glu Lys Asp Arg Thr Asn Gln Thr Gly Val Glu Pro
            20                  25                  30

Cys Tyr Gly Asp Lys Asp Lys Arg His Cys Phe Ala Thr Trp Lys
        35                  40                  45

Asn Ile Ser Gly Ser Ile Glu Ile Val Lys Gln Gly Cys Trp Leu Asp
    50                  55                  60

Asp Ile Asn Cys Tyr Asp Arg Thr Asp Cys Val Glu Lys Lys Asp Ser
65                  70                  75                  80

Pro Glu Val Tyr Phe Cys Cys Cys Glu Gly Asn Met Cys Asn Glu Lys
                85                  90                  95

Phe Ser Tyr Phe Pro Glu Met Glu Val Thr Gln Pro Thr Ser Asn Pro
            100                 105                 110

Val Thr Pro Lys Pro Pro His His His His His
            115                 120

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ser Ile Thr Ser Gly Tyr Tyr Trp Asn
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Ser Tyr Asp Gly Ser Asn Asn Tyr Asn Pro Ser Leu Ile Asn
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ala Tyr Arg Asn Asp Val Arg Phe Ala Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Arg Ala Ser Gln Asp Ile Ser Asn Phe Leu Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Thr Ser Arg Leu His Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Gly Asn Thr Leu Pro Trp Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Val Gln Leu Gln Glu Ser Ser Gly Pro Gly
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Gln Met Thr Gln Thr Thr Ser
1               5

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30
```

Tyr Tyr Trp Asn Trp Ile Arg Gln Phe Pro Gly Asn Lys Leu Glu Trp
            35                  40                  45

Met Gly Tyr Ile Ser Tyr Asp Gly Ser Asn Asn Tyr Asn Pro Ser Leu
 50                  55                  60

Ile Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Phe Cys
                85                  90                  95

Ala Ser Tyr Ala Tyr Arg Asn Asp Val Arg Phe Ala Tyr Trp Gly Gln
            100                 105                 110

Gly Thr Leu Val Thr Val Ser Ala
        115                 120

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 14
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gatgtacagc ttcaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tacataagct acgacggcag caataactac     180
aacccatctc tcataaatcg aatctccatc actcgtgaca catctaagaa ccagtttttc     240
ctgaagttga attctgtgac tactgaagac acagctacat atttctgtgc aagttatgcc     300
tataggaacg acgtgaggtt tgcttactgg ggccaaggga ctctggtcac cgtctccgca     360

<210> SEQ ID NO 15
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
gatatccaga tgacacagac tacatcctcc ctgtctgcct ctctgggaga cagagtcacc      60
atcagttgca gggcaagtca ggacattagc aattttttaa actggtatca gcagaaacca     120
gatggaactg ttaaactcct gatctacttc acatcaagat tacactcagg agtcccatca     180
aggttcagtg gcagtgggtc tggaacagat tattctctca ccattaccaa cctggagcaa     240
gaagatattg ccacttactt tgccaacag ggtaatacgc ttccgtggac gttcggtgga      300
ggcaccaagc tcgagatcaa a                                               321
```

<210> SEQ ID NO 16
<211> LENGTH: 116
<212> TYPE: PRT
<213> ORGANISM: Homo sapiens

<400> SEQUENCE: 16

```
Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Pro
        115
```

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Glu Val Lys Leu
1
```

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Asp Val Gln Leu
1
```